(12) United States Patent
Hollis et al.

(10) Patent No.: US 12,402,915 B2
(45) Date of Patent: Sep. 2, 2025

(54) BUNION CORRECTION SYSTEM AND METHOD

(71) Applicant: CrossRoads Extremity Systems, LLC, Memphis, TN (US)

(72) Inventors: Chad Hollis, Collierville, TN (US); Daniel Sayger, Southaven, MS (US); Bradley Bomar, Memphis, TN (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 502 days.

(21) Appl. No.: 17/632,786

(22) PCT Filed: Aug. 6, 2020

(86) PCT No.: PCT/US2020/045210
§ 371 (c)(1),
(2) Date: Feb. 3, 2022

(87) PCT Pub. No.: WO2021/026357
PCT Pub. Date: Feb. 11, 2021

(65) Prior Publication Data
US 2022/0409248 A1 Dec. 29, 2022

Related U.S. Application Data

(60) Provisional application No. 62/883,819, filed on Aug. 7, 2019.

(51) Int. Cl.
*A61B 17/56* (2006.01)
*A61B 17/00* (2006.01)
(Continued)

(52) U.S. Cl.
CPC .......... *A61B 17/56* (2013.01); *A61B 17/1659* (2013.01); *A61B 17/7233* (2013.01);
(Continued)

(58) Field of Classification Search
CPC ............ A61B 17/7233; A61B 17/7291; A61B 17/8061; A61B 17/809
See application file for complete search history.

(56) References Cited

U.S. PATENT DOCUMENTS

| 5,087,260 A | * | 2/1992 | Fixel | ............. A61B 17/746 606/65 |
| 5,531,678 A | | 7/1996 | Tomba et al. | |

(Continued)

FOREIGN PATENT DOCUMENTS

| DE | 202005012942 U1 | 10/2005 |
| EM | 005949237-0001 | 1/2019 |

(Continued)

OTHER PUBLICATIONS

International Search Report and Written Opinion for PCT Application No. PCT/US2020/043525 dated Dec. 7, 2020 in 22 pages.

(Continued)

*Primary Examiner* — Eduardo C Robert
*Assistant Examiner* — Anna V. Little
(74) *Attorney, Agent, or Firm* — BakerHostetler

(57) ABSTRACT

A minimally invasive method of correcting a bunion includes performing an osteotomy to divide the metatarsal into first and second portions, creating a pocket in the first portion implanting a nail in the pocket, securing a suture to the joint capsule, tensioning the suture to align the great toe with the metatarsal, attaching the suture to the nail, and fastening the nail to the second portion. The nail includes an anchor portion for anchoring in the first portion, a head for attachment to a second portion, a passage for attachment of the suture, a first aperture for a fastener to attach the head with the first portion, and a second aperture for a fastener to attach the head with the second portion.

14 Claims, 20 Drawing Sheets

(51) Int. Cl.
  *A61B 17/16* (2006.01)
  *A61B 17/72* (2006.01)
  *A61B 17/84* (2006.01)
  *A61B 17/86* (2006.01)

(52) U.S. Cl.
  CPC ...... *A61B 17/7283* (2013.01); *A61B 17/7291* (2013.01); *A61B 17/848* (2013.01); *A61B 17/86* (2013.01); *A61B 2017/00477* (2013.01); *A61B 2017/565* (2013.01)

(56) References Cited

U.S. PATENT DOCUMENTS

| | | | |
|---|---|---|---|
| 5,665,091 A | 9/1997 | Noble et al. | |
| 5,667,510 A | 9/1997 | Combs | |
| 5,810,822 A * | 9/1998 | Mortier | A61B 17/809 606/101 |
| 6,248,109 B1 | 6/2001 | Stoffella | |
| 6,379,359 B1 | 4/2002 | Dahners | |
| 6,656,182 B1 | 12/2003 | Hayhurst | |
| 6,689,136 B2 | 2/2004 | Stoffella | |
| 7,909,880 B1 | 3/2011 | Grant | |
| 8,231,625 B2 | 7/2012 | Graham et al. | |
| 8,343,152 B2 | 1/2013 | Gonzalez-Hernandez | |
| 8,460,343 B2 | 6/2013 | Graham | |
| 8,556,946 B2 | 10/2013 | Prandi et al. | |
| 8,986,353 B2 | 3/2015 | Johnson et al. | |
| 9,005,255 B2 | 4/2015 | Lewis et al. | |
| 9,060,822 B2 | 6/2015 | Lewis et al. | |
| 9,572,607 B2 | 2/2017 | Johnson et al. | |
| 9,888,949 B2 | 2/2018 | Johnson et al. | |
| 9,949,744 B2 | 4/2018 | Mccormick | |
| 10,022,170 B2 | 7/2018 | Leemrijse et al. | |
| 10,064,667 B2 | 9/2018 | Leemrijse et al. | |
| 10,213,236 B2 | 2/2019 | Lewis et al. | |
| 10,881,436 B2 | 1/2021 | Muller et al. | |
| 11,020,148 B2 | 6/2021 | Hollis et al. | |
| 2002/0143337 A1 | 10/2002 | Orbay et al. | |
| 2003/0040750 A1 | 2/2003 | Stoffella | |
| 2004/0111090 A1 | 6/2004 | Dahners | |
| 2005/0033302 A1 | 2/2005 | Frank | |
| 2008/0015593 A1 | 1/2008 | Pfefferle et al. | |
| 2009/0036931 A1 | 2/2009 | Pech et al. | |
| 2010/0274293 A1 | 10/2010 | Terrill et al. | |
| 2011/0257652 A1 | 10/2011 | Roman | |
| 2012/0016428 A1 | 1/2012 | White et al. | |
| 2012/0065638 A1 | 3/2012 | Moore | |
| 2012/0245633 A1 | 9/2012 | Schlotterback et al. | |
| 2012/0303033 A1 | 11/2012 | Weiner et al. | |
| 2013/0172942 A1 | 7/2013 | Lewis et al. | |
| 2015/0327900 A1 | 11/2015 | Toro et al. | |
| 2016/0074079 A1 * | 3/2016 | Leemrijse | A61B 17/809 606/291 |
| 2016/0199113 A1 | 7/2016 | Penzimer | |
| 2016/0213384 A1 | 7/2016 | Fallin et al. | |
| 2016/0354127 A1 | 12/2016 | Lundquist et al. | |
| 2017/0049576 A1 | 2/2017 | Guilford et al. | |
| 2017/0100176 A1 * | 4/2017 | Kumar | A61B 17/82 |
| 2017/0164989 A1 | 6/2017 | Weiner et al. | |
| 2017/0164990 A1 * | 6/2017 | Weiner | A61B 17/8014 |
| 2017/0172638 A1 | 6/2017 | Santrock et al. | |
| 2017/0196602 A1 * | 7/2017 | Lundquist | A61B 17/8061 |
| 2018/0028242 A1 * | 2/2018 | Parekh | A61B 17/8095 |
| 2018/0070995 A1 | 3/2018 | Kay et al. | |
| 2018/0161080 A1 | 6/2018 | Johnson et al. | |
| 2018/0214163 A1 | 8/2018 | Mccormick | |
| 2019/0125418 A1 * | 5/2019 | Muller | A61B 17/1604 |
| 2020/0015865 A1 | 1/2020 | Lamm et al. | |
| 2020/0253650 A1 | 8/2020 | Lamm et al. | |
| 2021/0022879 A1 | 1/2021 | Hollis et al. | |
| 2021/0077162 A1 | 3/2021 | Muller et al. | |

FOREIGN PATENT DOCUMENTS

| | | | |
|---|---|---|---|
| EP | 1952776 A1 | 8/2008 | |
| EP | 2228026 A1 | 9/2010 | |
| EP | 3476319 A2 | 5/2019 | |
| FR | 2878431 A1 | 6/2006 | |
| JP | 2003-093400 A | 4/2003 | |
| JP | 2019-080918 A | 5/2019 | |
| KR | 10-2015-0107824 A | 9/2015 | |
| WO | 2012/112642 A1 | 8/2012 | |
| WO | WO-2016033311 A1 * | 3/2016 | ......... A61B 17/1728 |
| WO | 2017/011589 A1 | 1/2017 | |
| WO | 2019/231531 A1 | 12/2019 | |
| WO | 2020/041841 A1 | 3/2020 | |
| WO | 2021/021640 A1 | 2/2021 | |
| WO | 2021/026357 A1 | 2/2021 | |

OTHER PUBLICATIONS

International Search Report and Written Opinion in PCT/US2020/045210 dated Oct. 26, 2020.
US. Appl. No. 61/086,822, filed Aug. 7, 2008, Gonzalez-Harnandez et al.

* cited by examiner

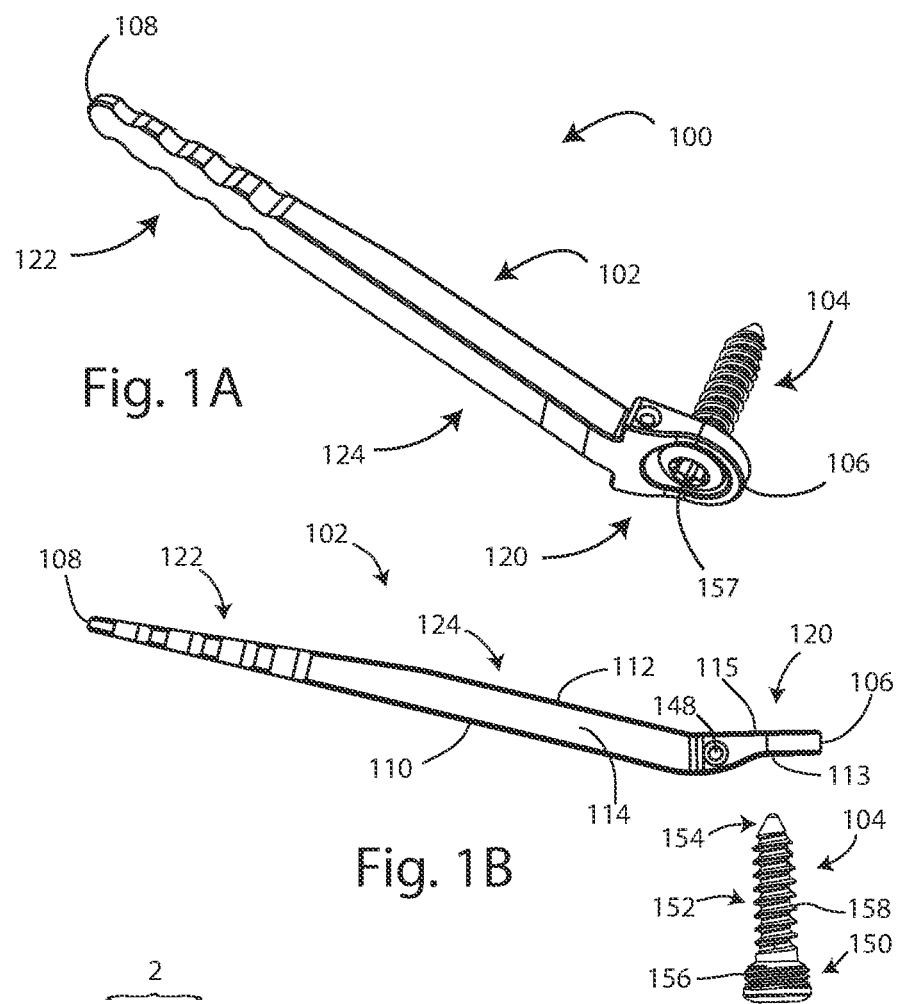
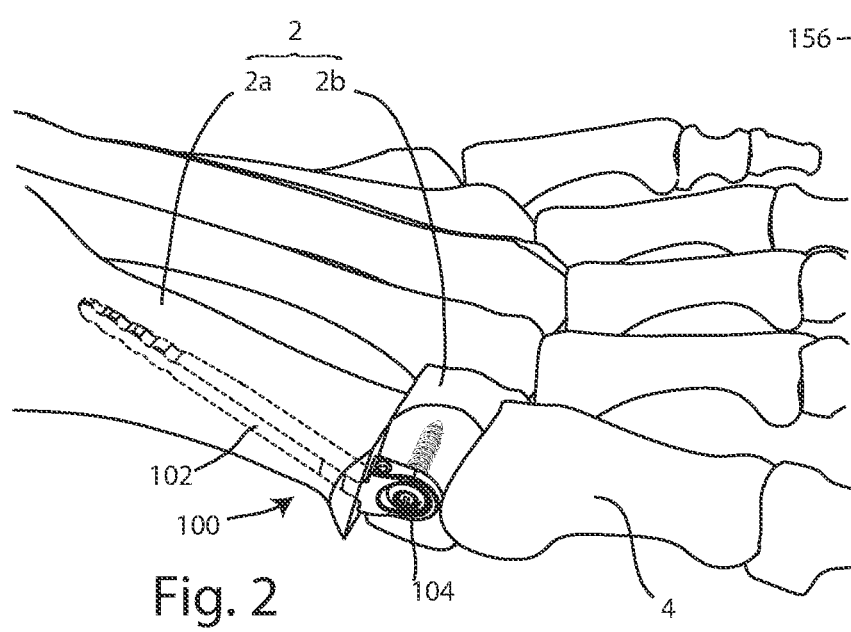

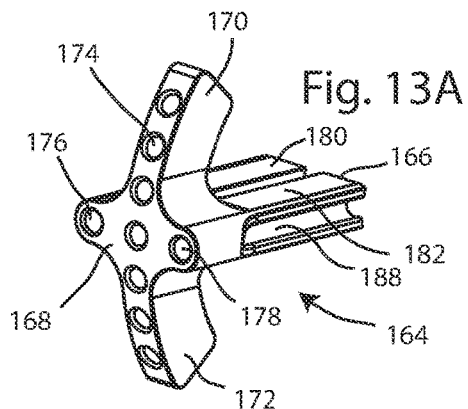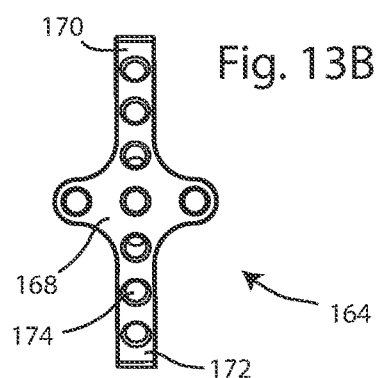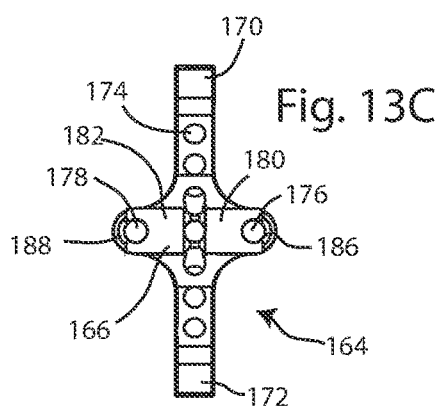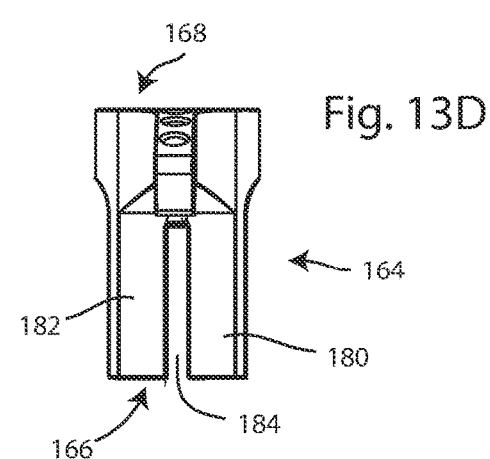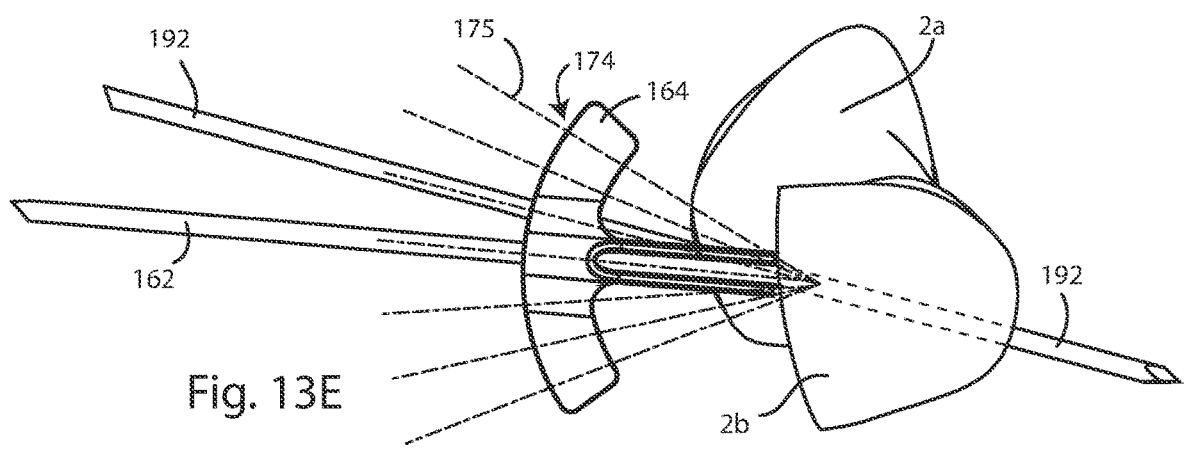

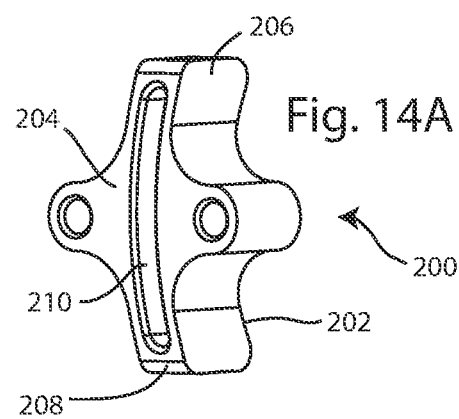
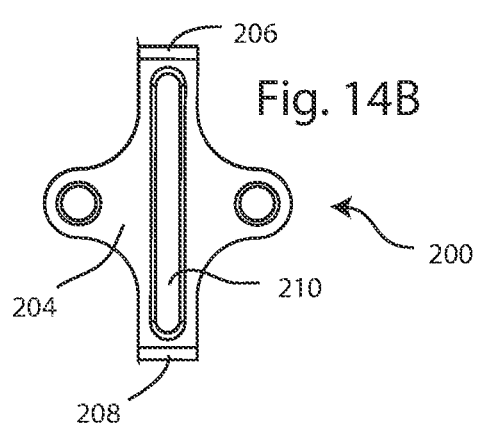
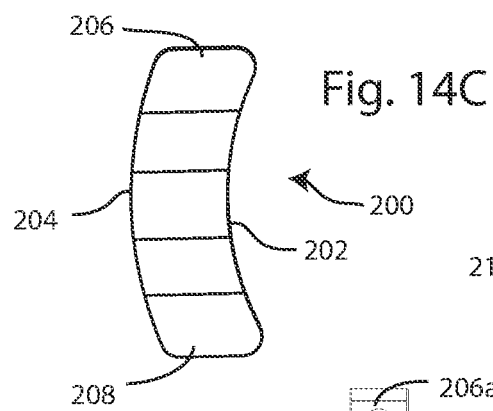
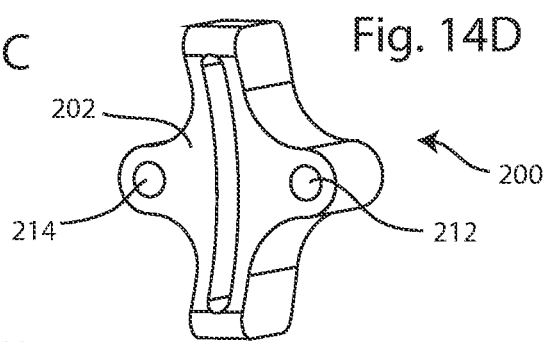
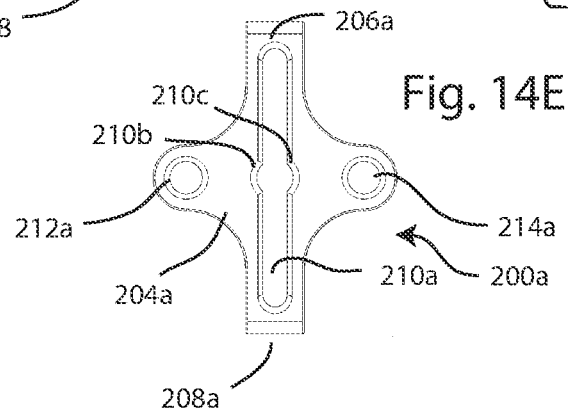
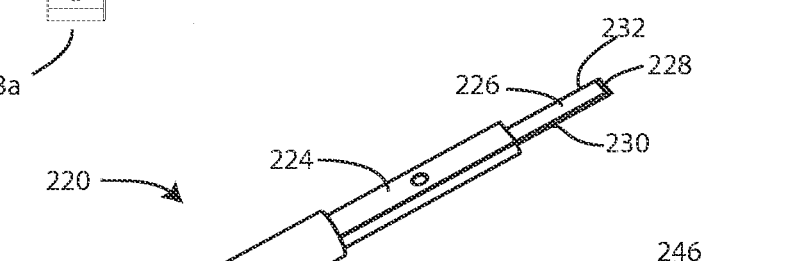
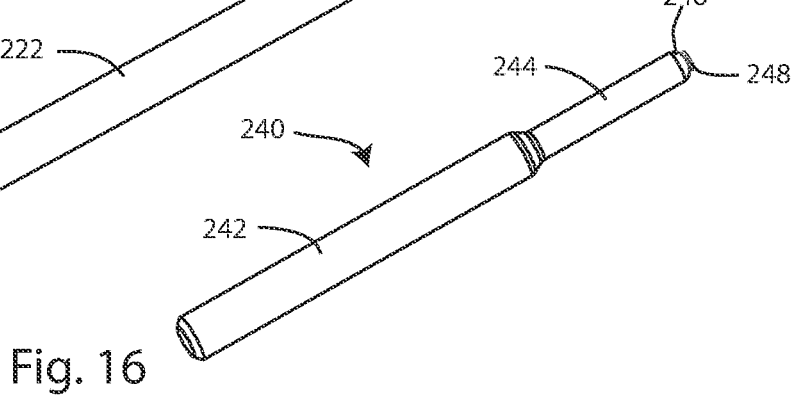

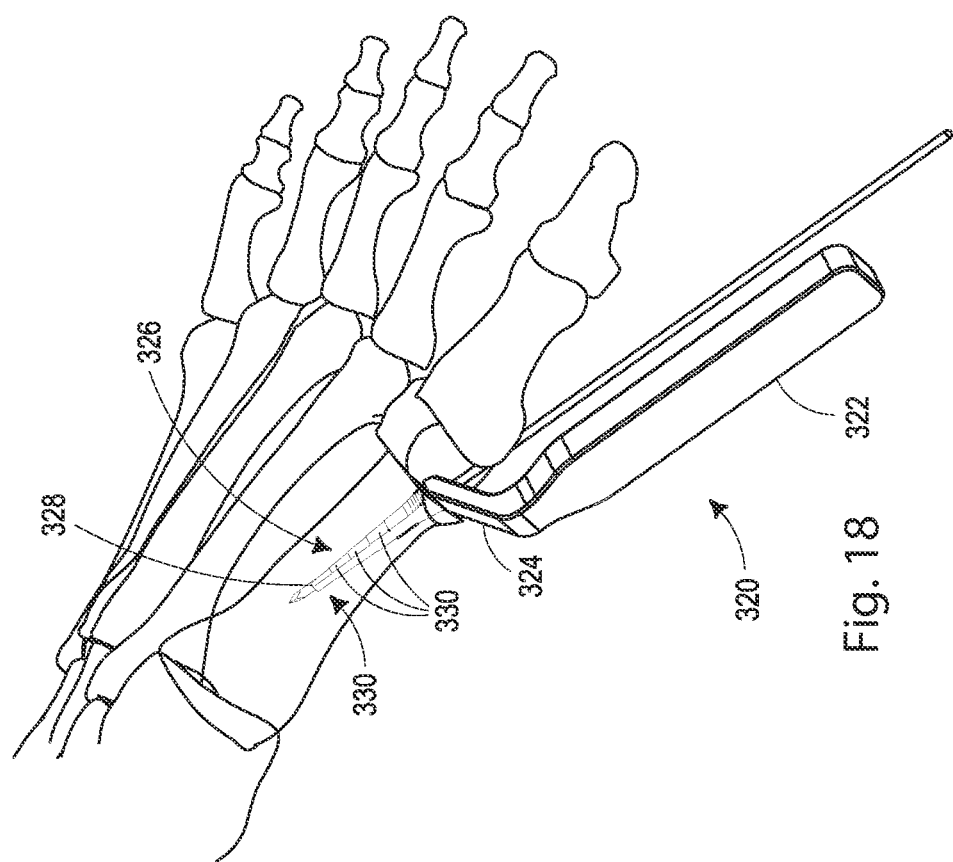

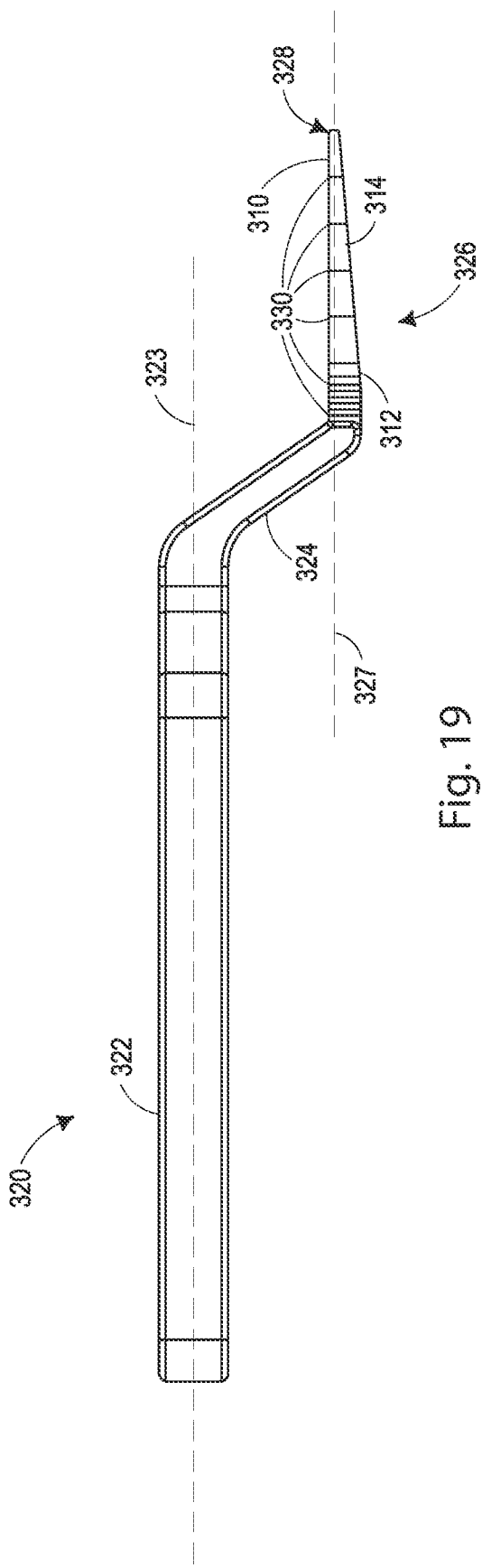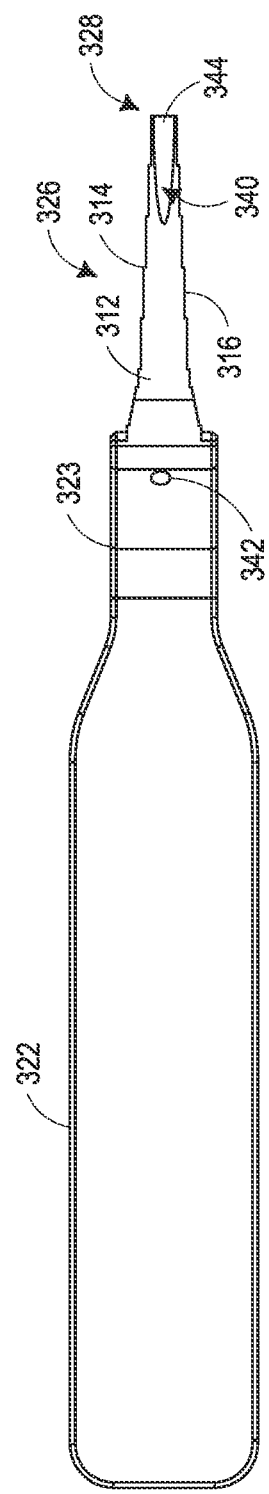

BUNION CORRECTION SYSTEM AND METHOD

INCORPORATION BY REFERENCE TO ANY RELATED APPLICATIONS

The is a national phase application of PCT Application No. PCT/US2020/045210, filed Aug. 6, 2020, which claims the benefit of U.S. Provisional Patent Application No. 62/883,819, titled "BUNION CORRECTION SYSTEM AND METHOD," filed Aug. 7, 2019, the entirety of which is hereby incorporated by reference.

FIELD

The present invention relates to surgical treatment for deformities of the foot. More specifically, the present invention relates to implants, instrumentation and methods for minimally invasive bunion correction.

BACKGROUND

Bunions are a progressive disorder typically beginning with a leaning of the great toe, which may gradually change the angle of the bones and produce a characteristic bump on the medial side of the metatarsal near the joint of the metatarsal with the proximal phalanx. Specifically, the bunion is the prominence made of bone and at times an inflamed bursa. Hallux valgus is the condition in which the great toe deviates from the normal position toward the direction of the second toe.

Bunion correction or repair is a common surgery with over 100,000 surgeries performed annually in the US. Many surgical procedures for bunion repair are invasive and painful, requiring an incision of several inches and a long period of convalescence, of up to 10-12 weeks. Minimally invasive surgery has been performed in orthopedics for decades. However, creating the bone cuts has been performed with burrs and drill bits inserted blindly through small incisions. This method of surgery lends itself to potential adjacent soft tissue damage and unrepeatable results from patient to patient. The disclosure contained herein seeks to remedy this problem by providing an instrumented technique and guides to provide repeatability and limit the damage to tissue along with a simple implant insertion technique.

Disclosed herein is an implant and method for bunion repair which can be performed as a minimally invasive procedure, thus reducing discomfort, scarring and recovery time in comparison with more invasive bunion correction procedures.

SUMMARY OF THE INVENTION

The various systems and methods of the present invention have been developed in response to the present state of the art, and in particular, in response to the problems and needs in the art that have not yet been fully solved by currently available techniques. The systems and methods of the present invention may provide techniques for bunion correction which result in a streamlined procedure, faster recovery, reduced scarring, and reduced discomfort during healing.

To achieve the foregoing, and in accordance with the invention as embodied and broadly described herein, one aspect of the disclosure is a first method for correcting a bunion formed at the joint between a metatarsal and a great toe. An incision is made along a side of the metatarsal. A target location is selected on the metatarsal. The metatarsal is resected into a first metatarsal portion and a separate second metatarsal portion at the target location. The first metatarsal portion has a distal-facing surface created by the resecting. A pocket instrument is inserted into the first metatarsal portion at the distal-facing surface to create a pocket in the first metatarsal portion at the distal-facing surface. An implant is inserted through the incision into the pocket of the first metatarsal portion, the implant having a monolithic body with a head and an anchor.

In another aspect of the first method, the pocket extends into an intramedullary canal of the first metatarsal portion through the distal-facing surface.

In another aspect of the first method, at least one k-wire inserts into the first metatarsal portion through the distal-facing surface. The first k-wire guides the first instrument into the first metatarsal portion to create the pocket.

In another aspect of the first method, the first pocket instrument is a broach.

In another aspect of the first method, the broach includes a handle aligned along a first axis, a insertion portion having a plurality of teeth aligned along a second axis, and an offset portion between the handle and the insertion portion such that the first axis is angled with respect to the second axis.

In another aspect of the first method, the implant head attaches to the first metatarsal portion.

In another aspect of the first method, the implant head attached to the first metatarsal portion includes inserting a screw through an aperture of the implant head and into the first metatarsal portion.

In another aspect of the first method, the implant head attaches to the second metatarsal portion.

In another aspect of the first method, a length of suture is secured to the great toe, tensioning the suture to re-align the great toe relative to the first metatarsal portion, and attaching the length of suture to the implant head.

In another aspect of the first method, the second metatarsal portion translates to expose the distal-facing surface on the first metatarsal portion.

Another aspect of the disclosure is a second method for correcting a bunion. An incision is made along a side of the metatarsal. A target location is selected on the metatarsal. The metatarsal is resected into a first metatarsal portion and a separate second metatarsal portion, the first metatarsal portion having a distal-facing surface created by the resecting. An implant is implanted through the incision into the first metatarsal portion. The implant has a monolithic body having a head and an anchor, the anchor extending along an implant axis. The implant head is firstly attached to the first metatarsal portion at the distal-facing surface; and the implant head is secondly attached to the second metatarsal portion.

In another aspect of the second method, the implant head is attached to the first metatarsal portion and includes inserting a first screw through a first aperture of the implant head and into the distal-facing surface of the first metatarsal portion.

In another aspect of the second method, the first aperture is aligned along a first axis at a first angle relative to the implant axis.

In another aspect of the second method, the first angle is less than approximately 45°.

In another aspect of the second method, attaching the implant head to the second metatarsal portion includes inserting a second screw through a second aperture of the implant head and into the second metatarsal portion.

In another aspect of the second method, the second aperture is aligned along a second axis at a second angle relative to the implant axis, the second angle being greater than the first angle.

In another aspect of the second method, the second angle is greater than 60°.

In another aspect of the second method, the second metatarsal portion translates to expose the distal-facing surface on the first metatarsal portion. A pocket is created in the first metatarsal portion at the distal-facing surface, and the pocket extends into an intramedullary canal of the first metatarsal portion through the distal-facing surface.

In another aspect of the second method, a pocket instrument is inserted and guided by at least one k-wire into the first metatarsal portion at the distal-facing surface to create the pocket.

In another aspect of the second method, a length of suture is secured to the great toe, tensioning the suture to re-align the great toe relative to the first metatarsal portion, and attaching the length of suture to the implant.

Another aspect of the disclosure is a third method for correcting a bunion. An incision is made along a side of the metatarsal. A first k-wire is introduced through the incision and into the metatarsal at a selected target location. The metatarsal is resected into a first metatarsal portion and a separate second metatarsal portion at the selected target location. The first metatarsal portion has a distal-facing surface created by the resecting. A second k-wire is inserted into the first metatarsal portion at the distal-facing surface. A pocket instrument is inserted into the first metatarsal portion at the distal-facing surface guided by the second k-wire to create a pocket in the first metatarsal portion at the distal-facing surface. An implant is inserted through the incision into the first metatarsal portion, the implant having a monolithic body having a head and an anchor, the anchor extending along an implant axis. The implant head is attached to the first metatarsal portion at the distal-facing surface and attaching the implant head to the second metatarsal portion.

In another aspect of the third method, attaching the implant head to the first metatarsal portion includes inserting a first screw through a first aperture of the implant head and into the distal-facing surface of the first metatarsal portion and attaching the implant head to the second metatarsal portion includes inserting a second screw through a second aperture of the implant head and into the second metatarsal portion.

In another aspect of the third method, the second metatarsal portion translates to expose the distal-facing surface on the first metatarsal portion; and a pocket is created in the first metatarsal portion at the distal-facing surface, wherein the pocket extends into an intramedullary canal of the first metatarsal portion through the distal-facing surface.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

FIG. 1A is a perspective view of a bunion correction implant, comprising a nail and a fastener, according to one embodiment of the invention; FIG. 1B is an exploded view of the implant;

FIG. 2 is a perspective view of a partial skeleton of a foot, with the implant of FIG. 1A implanted into the first metatarsal;

FIG. 13A is a perspective view of the first guide of FIG. 5; FIG. 13B is a medial view of the first guide of FIG. 5; FIG. 13C is a lateral view of the first guide of FIG. 5; FIG. 13D is a superior view of the first guide of FIG. 5; FIG. 13E is a distal view of the distal end of the metatarsal, the first guide, and the trocar of FIG. 6 extending through another one of the guide holes, with dotted lines indicating the trajectories of the plurality of guide holes;

FIG. 14A is a medial perspective view of the second guide of FIG. 7;

FIG. 14B is a medial view of the second guide of FIG. 7;

FIG. 14C is a side view of the second guide of FIG. 7;

FIG. 14D is a lateral perspective view of the second guide of FIG. 7;

FIG. 14E is a medial view of another embodiment of a second guide;

FIG. 15 is a perspective view of the broach of FIG. 8;

FIG. 16 is a perspective view of the implant inserter of FIG. 10;

FIG. 18 is a perspective view of the foot skeleton of FIG. 17, showing a pocket instrument for forming a pocket inserted into the proximal metatarsal portion as guided by the k-wire;

FIG. 19 is a side view of the pocket instrument shown in FIG. 18;

FIG. 20 is a bottom view of the pocket instrument shown in FIG. 18;

DETAILED DESCRIPTION

Figure 3A:
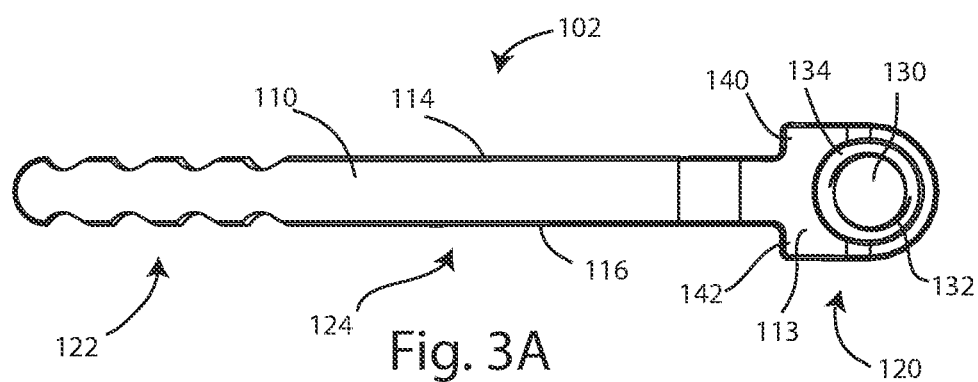
FIG. 3A is medial view of the nail of FIG. 1A.

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1A through 25, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

Directional and/or relational terms such as, but not limited to, left, right, superior, inferior, top, bottom, vertical, horizontal, medial, and lateral are relative to each other, are dependent on the specific orientation of an applicable element or article, are used accordingly to aid in the description of the various embodiments in this specification and the appended claims, and are not necessarily intended to be construed as limiting. Standard medical terminology may be used to describe human anatomy, or the relationship of objects to the human anatomy. For example, proximal refers to an object or anatomical element closer to the center of the body, while distal refers to an object or anatomical element farther away from the center of the body.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Referring to FIG. 1A, a bunion correction implant system 100 according to one embodiment of the invention includes a nail 102 and a fastener 104. As seen in FIG. 2, the nail 102 may be implanted to extend longitudinally into a proximal portion 2a of a resected metatarsal 2, and the fastener 104 inserted through a portion of the nail to secure it to the distal portion 2b of the metatarsal 2. The bunion correction implant system 100 may further include a suture which may be routed through the medial capsule of the metatarsophalangeal (MTP) joint, secured in the soft tissues of the great toe, tensioned to re-align the position of the proximal phalanx 4 relative to the metatarsal, and secured to the nail.

Referring to FIGS. 1A-B, and 3A-C, the implant nail 102 is a monolithic body extending from a first end 106 which may be a distal end, to a second end 108 which may be a proximal end. The nail 102 may be generally rectangular in cross-section, having a medial side 110 which may be an outer side, a lateral side 112 which may be an inner side, a superior side 114, and an inferior side 116. The nail 102 includes a head 120, an anchor 122, and a neck 124 extending between the head 120 and the anchor 122.

Figure 3B:
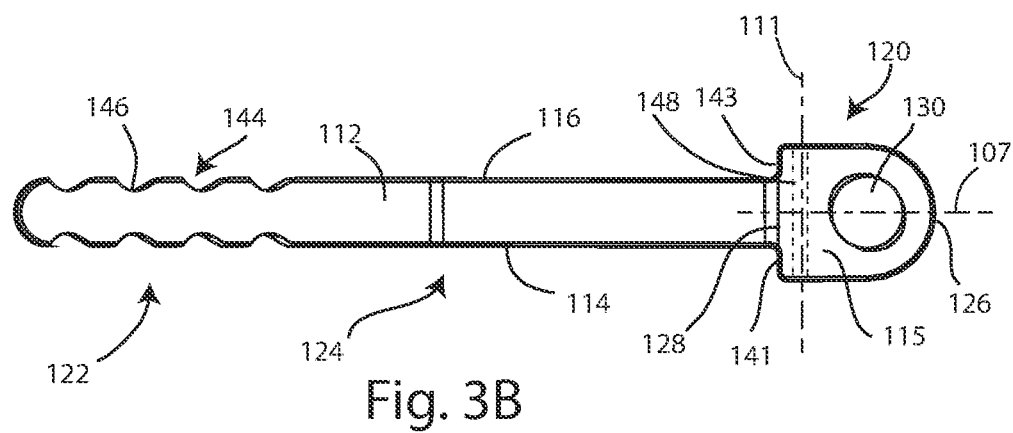
FIG. 3B is lateral view of the nail of FIG. 1A.
Figure 3C:
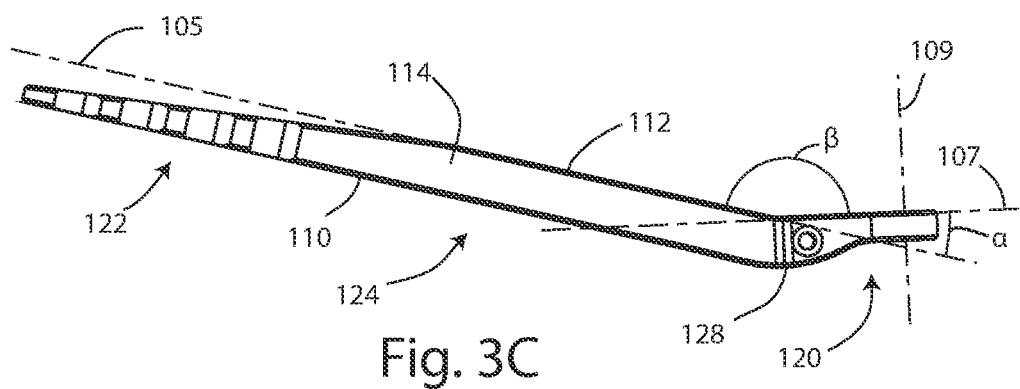
FIG. 3C is a superior view of the nail of FIG. 1A.

With particular reference to FIGS. 3B and 3C, the nail anchor 122 and neck 124 extend along a longitudinal axis 105, and the nail head 120 extends distally away from the neck 124 at an angle. The nail head extends between a head first end 126 and a head second end 128 along a head first axis 107. In the embodiment depicted, the angle $\alpha$ between the head first axis 107 and the longitudinal axis 105 is 15°, with an angle $\beta$ between the neck lateral surface and the head lateral surface of 165°. In other embodiments of the invention, angle $\alpha$ may be in the range of 0° to 25°. In at least the embodiment depicted, the nail 102 and assembled implant 100 are bilaterally symmetrical with respect to the longitudinal axis 105, and with respect to the head first axis 107.

The nail head 120 includes an opening 130 centered on a head second axis 109, which is perpendicular to the head first axis 107. The head second axis may extend generally medially-laterally (ML) upon implantation. In the embodiment depicted, the opening 130 extends between a head lateral side 115 and a head medial side 113, and includes threads 132 for engagement with the fastener 104, although additional embodiments may lack threads. A concave lip 134 encircles the opening 130. The head second end 128 is wider than the neck 124 with respect to the superior-inferior dimension, and includes a first shoulder 140 and a second shoulder 142, the shoulders 140, 142 projecting superiorly and inferiorly, respectively, away from the neck 124 at the intersection of the neck and the head. The first shoulder 140 includes a first proximal shoulder surface 141, and the second shoulder 142 includes a second proximal shoulder surface 143. The proximal shoulder surfaces 141, 143 face proximally away from the head 120 and are at right angles to the neck superior and inferior sides 114, 116. The head 120 may further include a transverse bore 148, extending along a head third axis 111 which is perpendicular to the head first axis 107 and the head second axis 109. The head third axis 111 may extend generally superiorly-inferiorly (SI) upon implantation. In the embodiment depicted, the thickness of the head 120 between its medial 113 and lateral 115 sides increases between the head first end 126 and the head second end 128, so that the thickest part of the head is at the shoulders 140, 142.

The neck 124 extends between and connects the head 120 with the anchor 122. The thickness of the neck 124 between the medial 110 and lateral 112 sides can vary depending on the desired degree of shift of the metatarsal. In at least the embodiment depicted, the neck thickness tapers between the head 120 and the anchor 122. The width of the neck 124 between the superior 114 and inferior 116 sides may also vary. The length of the nail between the first and second ends 106, 108 can vary, as can the relative lengths of the head, neck, and/or anchor portions. The anchor 122 is coaxial with the neck 124, and extends from the neck to the second end 108 of the nail. Both the thickness of the anchor between the medial 110 and lateral 112 sides, and the width of the anchor between the superior 114 and inferior 116 sides may taper towards the nail second end, promoting easy insertion of the nail into bone. The anchor second end may be rounded as in the embodiment depicted in FIGS. 1A and 1B; in other embodiments it may be pointed, flattened, serrated, or another shape. The anchor 122 includes a plurality of bone engagement features 144 which may be shaped as teeth, scallops, serrations, or other shapes to promote engagement within bone. For example, the scallops 146 in the embodiment depicted provide surface irregularities which resist nail backup. In the embodiment shown, the neck and anchor are free from openings; other embodiments could include openings for supplementary fixation or instrument connection.

Fastener 104 includes a fastener head 150, fastener shaft 152, and tip 154. The head 150 includes threads 156 for locking engagement with threads 132 in the nail head 120; other embodiments may lack threads 156. The shaft 152 includes threads 158 for engagement in bone. The head 150 may include a driving feature 157 for engagement with a driver. In the embodiment depicted, fastener 104 is a locking screw type fastener; in other embodiments the fastener may be locking or non-locking, and may be polyaxially adjustable or non-polyaxially adjustable.

The nail 102 and fastener 104 may comprise titanium, stainless steel, polyether ether ketone (PEEK), nitinol, and/or other rigid biocompatible materials or combinations thereof. The suture is a non-resorbable suture, although other embodiments may include a resorbable suture.

Referring to FIGS. 4-16, a method of correcting a bunion includes one or more of the following steps. Although the steps are described in an order, in other embodiments of the method one or more of the steps may be repeated, omitted, or performed in a different order.

Figure 4:
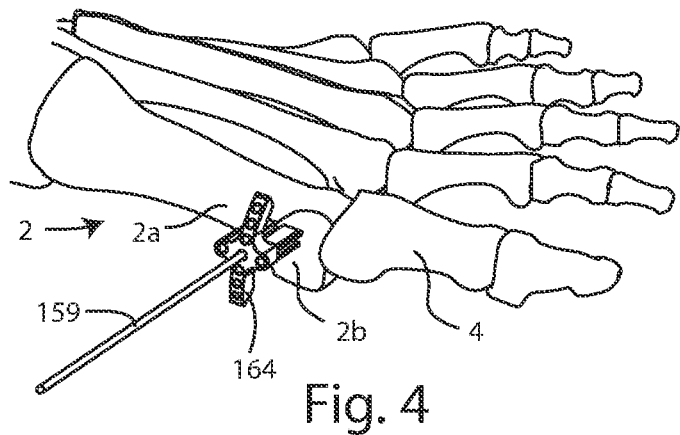
FIG. 4 is a perspective view of the foot skeleton with a k-wire inserted into the metatarsal and a first guide mounted on the k-wire, the first guide having a plurality of guide holes.
Figure 5:
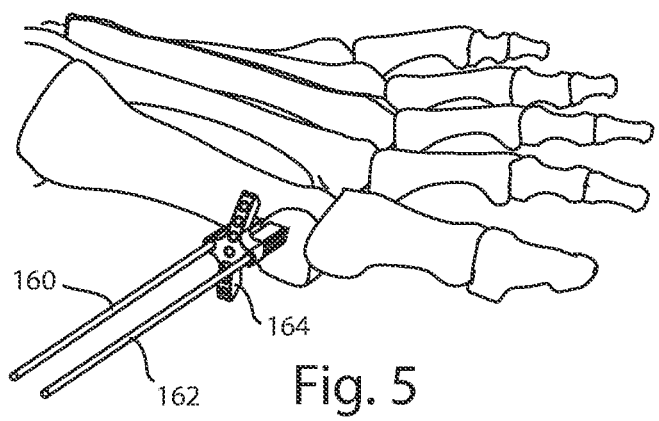
FIG. 5 is a perspective view of the foot skeleton, k-wire and guide of FIG. 4, with additional k-wires inserted into the metatarsal.

A small incision is made in the affected metatarsal at the medial side of the bunion. Preferably, the incision is 0.5 inch long or less. Referring to FIG. 4, a first k-wire 159 is introduced through the incision and into the metatarsal at a selected target location. A first guide block 164 is mounted onto the k-wire 159 and urged toward the metatarsal 2. Referring to FIG. 5, second and third k-wires 160, 162 are introduced through the guide block 164 into the metatarsal, on either side of the selected target location. The second k-wire 160 is located in a proximal metatarsal portion 2a, and the third k-wire 162 is introduced into a distal metatarsal portion 2b. The first k-wire 159 is removed from the metatarsal.

As shown in FIGS. 13A-E, the first guide block 164 extends between a first or lateral side 166, and a second or medial side 168. First and second guide portions 170, 172 project superiorly and inferiorly, respectively. A series of guide holes 174 extend through the guide block, each defining a trajectory 175, which converge at a common point, as seen in FIG. 13E. The guide holes 174 and their trajectories 175 are coplanar, defining a cut plane when the first guide block 164 is mounted on the k-wires 160, 162. A pair of mounting holes 176, 178 are sized to slide over the k-wires. First and second mounting supports 180, 182 extend medially from the guide block 164 and are separated by a gap 184. The mounting supports 180, 182 include slots 186, 188 for guiding and supporting the k-wires, and prevent rotation of the guide block 164 once mounted. The medial side 168 of the guide block 164 may be convexly curved as shown.

Figure 6:
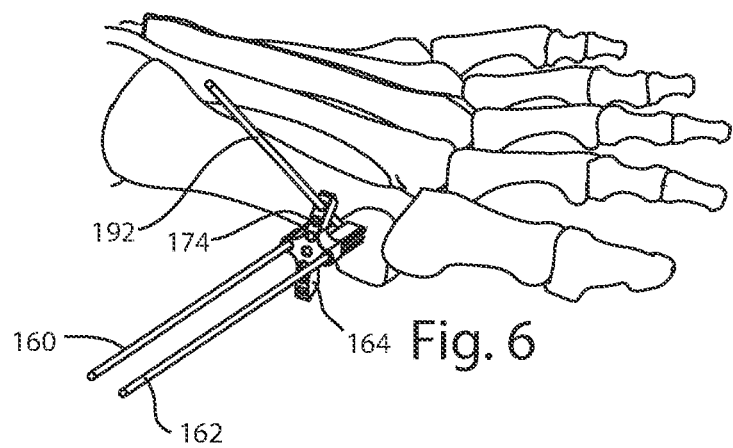
FIG. 6 is a perspective view of the foot skeleton, k-wires and first guide of FIG. 5, with a trocar extending through one of the guide holes to create a hole in the metatarsal.

Referring to FIGS. 6 and 13E, after the first guide block 164 is mounted on the k-wires and abuts the metatarsal 2, a trocar 192, reamer or other instrument is introduced through one of the guide holes 174 and inserted into the metatarsal 2 to create a hole through the metatarsal along the trajectory of the guide hole. The trocar 192 may then be inserted through more of the guide holes 174 and through the metatarsal. This step creates a linear series of openings through the bone at the targeted location, weakening the bone at that location in preparation for a subsequent osteotomy to resect the metatarsal head. After the desired number of openings are created, the first guide block 164 is withdrawn from the k-wires.

Figure 7:
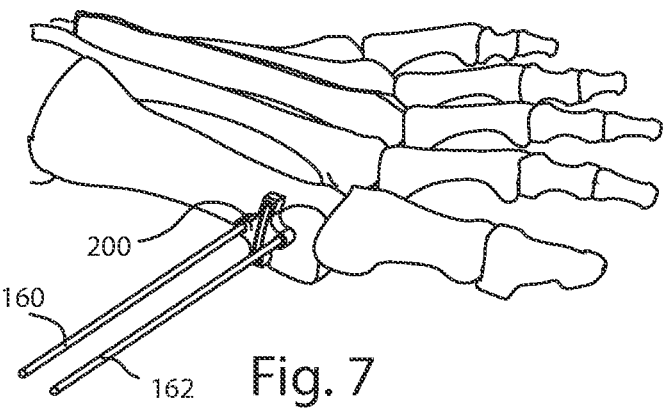
FIG. 7 is a perspective view of the foot skeleton and k-wires of FIG. 5, with a second guide mounted on the k-wires.

Referring to FIG. 7, a second guide block 200 is introduced onto the k-wires 160, 162. As shown in FIGS. 14A-D, the second guide block 200 extends between a first or lateral side 202, and a second or medial side 204. First and second guide portions 206, 208 project superiorly and inferiorly, respectively. A cutting slot 210 extends through the guide block 200, opening out on the lateral and medial sides 202, 204, and mounting holes 212, 214 extend between the medial and lateral sides for mounting the block on the k-wires. The guide block 200 may be curved as shown, wherein the medial side 204 of the guide block 200 is convexly curved and the lateral side 202 is concave. At least the concave lateral surface may allow the guide to fit closely against the targeted location. When the second guide block 200 is mounted on the k-wires 160, 162, the mid-plane of the opening defined by the cutting slot 210 is coplanar or at least parallel with the cut plane defined by the first guide block guide holes 174 and trajectories 175, and with the series of openings created in the bone in the previous step.

FIG. 14E shows an alternative embodiment of a second guide block 200a, similar to the second guide block 200 with the differences noted below. The second guide block 200a can extend between a first or medial side (204a) and a lateral side (not shown). The lateral side can be concave and the medial side 204a can be convex. A cutting slot 210a extends through the guide block 200a. The cutting slot 210a can include a first concave channel 210b on a first side of the cutting slot 210a and/or a second concave channel 210c on a second side of the cutting slot 210a. The channels 210b, 210c can form an aperture for receiving a k-wire (e.g., first k-wire 159). First and second guide portions 206a, 208a project superiorly and inferiorly from the cutting slot 210a. Mounting holes 212a, 214a extend between the medial and lateral sides. The second guide block 200a can be mounted first on a k-wire through the channels 210b, 210c and urged toward the metatarsal 2 (See FIG. 4). Second and third k-wires 160, 162 can then be introduced through the mounting holes 212a, 214a and into the metatarsal 2. The first k-wire 159 can then be removed from the metatarsal 2.

Figure 8:
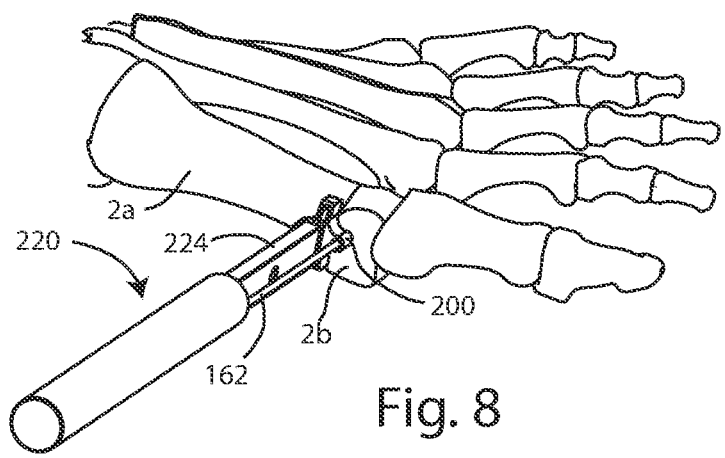
FIG. 8 is a perspective view of the foot skeleton, k-wires and second guide of FIG. 7, with a broach extending through a guide slot to cut an osteotomy in the metatarsal and separate the metatarsal into a proximal metatarsal portion and a distal metatarsal portion.

Referring to FIGS. 8 and 15, a broach 220 is used to create an osteotomy in the metatarsal 2, resecting the metatarsal into the first or proximal metatarsal portion 2a and the second or distal metatarsal portion 2b. The broach 220 includes a handle portion 222, a shaft portion 224, and a insertion portion 226 with a cutting tip 228 and cutting edges 230, 232. The cutting edges and tip may be beveled, sharpened, serrated and/or otherwise configured to cut through bone. The broach insertion portion 226 is urged laterally through the cutting slot 210 and into the bone to create the osteotomy. The shaft portion 224 may act as a stop to limit lateral insertion of the insertion portion through the cutting slot. In other embodiments of the method, instead of or in combination with broach 220, a saw, blade, chisel, osteotome, curette, pick, rasp or other instrument or combinations thereof may be used to perform the osteotomy. When the osteotomy step is completed, the second guide block 200 is removed from the k-wires. Similarly, a cutting instrument, such as those listed above, can be urged laterally through the cutting slot 210a of the second guide block 200a and into the bone to create the osteotomy.

Figure 9:
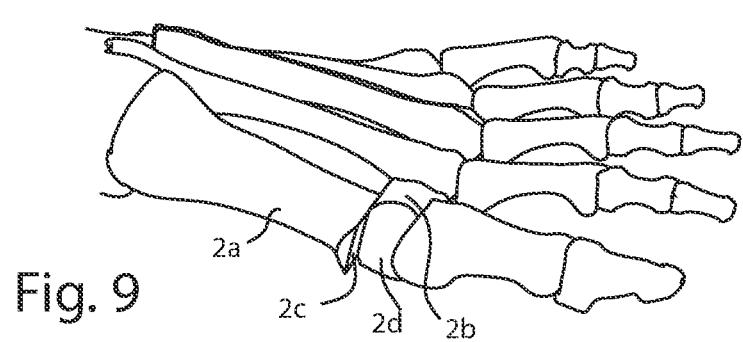
FIG. 9 is a perspective view of the foot skeleton of FIG. 8, with the distal metatarsal portion shifted laterally relative to the proximal metatarsal portion.

Referring to FIG. 9, the now separate distal metatarsal bone portion 2b is translated laterally relative to proximal metatarsal bone portion 2a. A generally flat distal-facing surface 2c on the proximal metatarsal portion 2a is exposed, and it is into this surface that the nail 102 is implanted. Distal-facing surface 2c of the proximal metatarsal bone portion 2a, and a medial-facing surface 2d of the distal metatarsal bone portion 2b may be referred to as abutment surfaces. The degree of offset of the distal metatarsal portion may vary but is sufficient to permit implantation of nail 102 into the distal-facing surface 2c so that the nail head 120 does not protrude medially beyond the medial outer surface of the proximal metatarsal portion 2a after implantation. The k-wires 160, 162 may be removed before or after the shifting of the distal metatarsal portion relative to proximal metatarsal portion.

Figure 10:
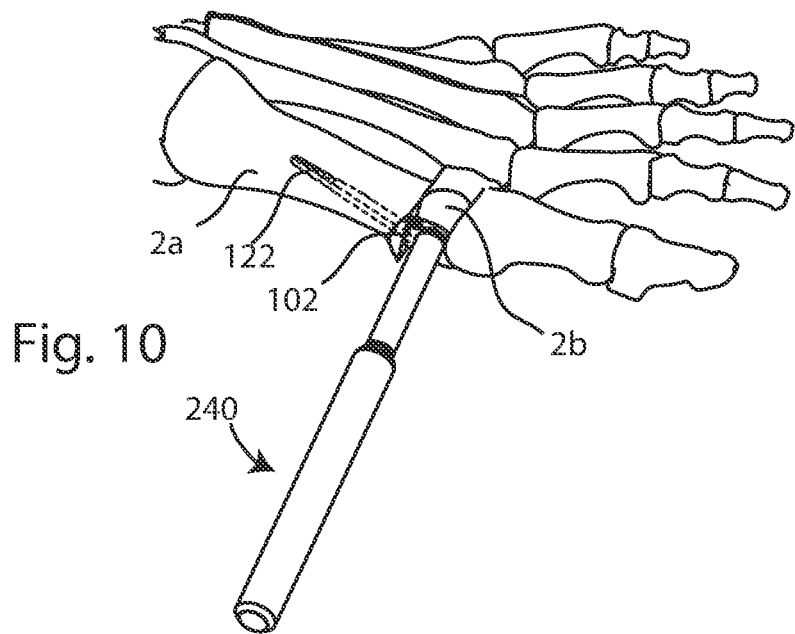
FIG. 10 is a perspective view of the foot skeleton of FIG. 9, with the nail of FIG. 1 mounted on an implant inserter and implanted into the proximal metatarsal portion.

Referring to FIGS. 10 and 16, the nail 102 is inserted through the incision and anchored into the prepared proximal metatarsal portion 2a. Prior to implantation, a suture 250 may be introduced to extend through the transverse bore 148. An implant inserter such as inserter 240 may be employed to implant the nail 102 into the bone. Inserter 240 comprises a handle portion 242, a shaft portion 244, and an implant engagement end 246. Threads 248 are formed on the implant engagement end 246, which may cooperate with the nail threads 132 to removably attach the nail 102 to the inserter 240. The inserter 240 is moved to insert the anchor 122 and neck 124 proximally into the distal-facing surface 2c and into the intramedullary canal of the metatarsal, leaving the head 120 distal to the proximal metatarsal portion 2a. If needed, the inserter 240 may be tapped to drive the nail 102 into position in the proximal metatarsal portion 2a. The nail 102 is positioned so that the proximal surfaces 141, 143 of shoulders 140, 142 abut the prepared distal-facing surface 2c of the metatarsal, and the nail head lateral side 115 is immediately adjacent to medial surface 2d of the distal metatarsal portion 2b. When the nail 102 is properly seated in the desired location, the inserter 240 may be rotated to disengage it from the implanted nail 102.

Figure 12:
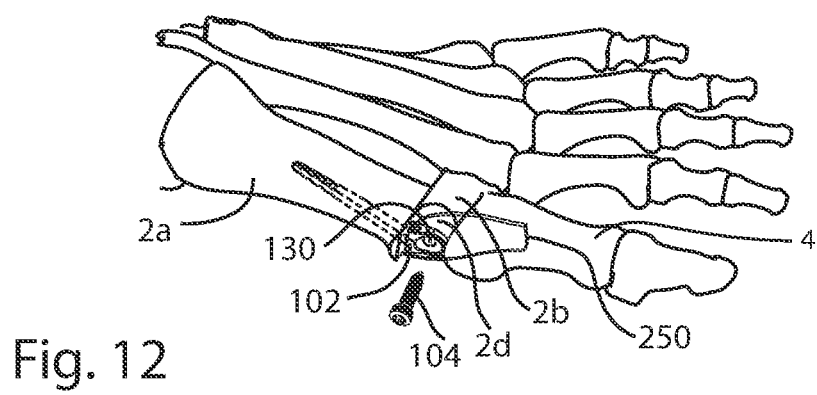
FIG. 12 is a perspective view of the foot skeleton of FIG. 10 showing the suture and the fastener aimed toward an opening of the nail.
Figure 11A:
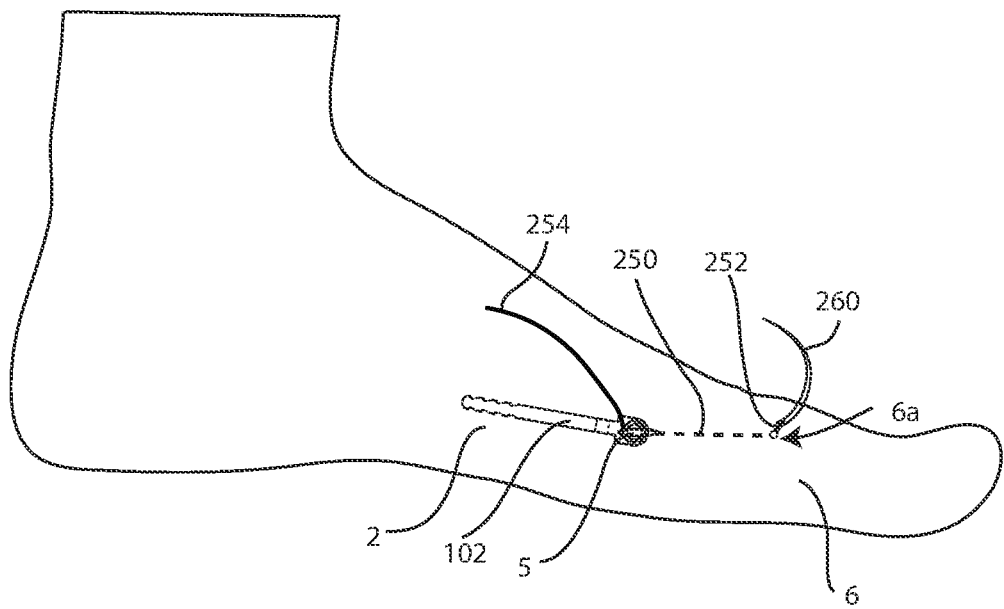
FIG. 11A is a medial view of the foot with the nail of FIG. 1 implanted in the proximal metatarsal portion and a needle and suture inserted into the foot through an incision at the site of the implant and exiting at a first location on the great toe at the proximal phalanx.
Figure 11B:
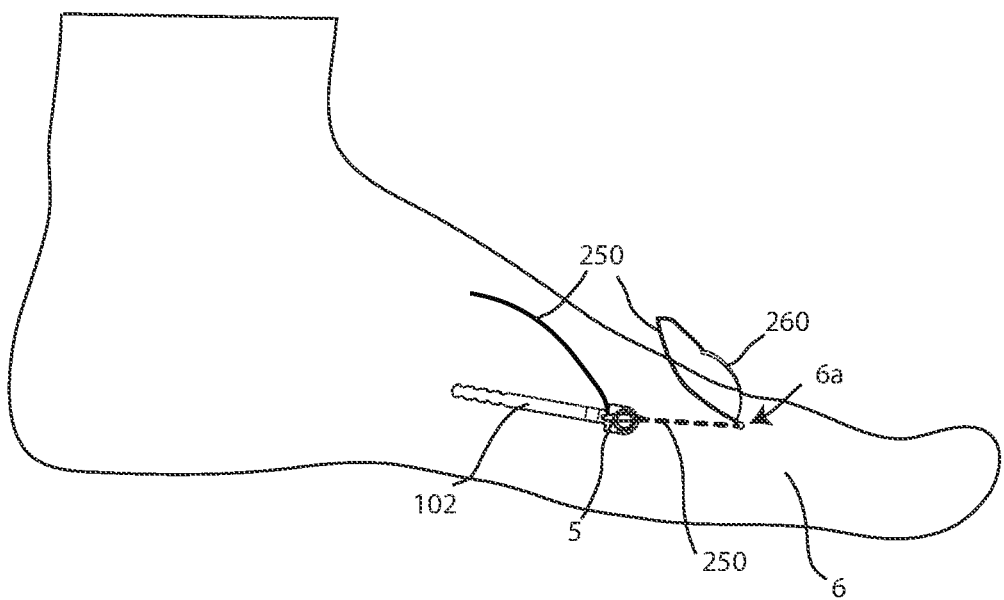
FIG. 11B is a medial view of the foot of FIG. 11A, with a first stitch being made at the first location on the great toe.
Figure 11C:
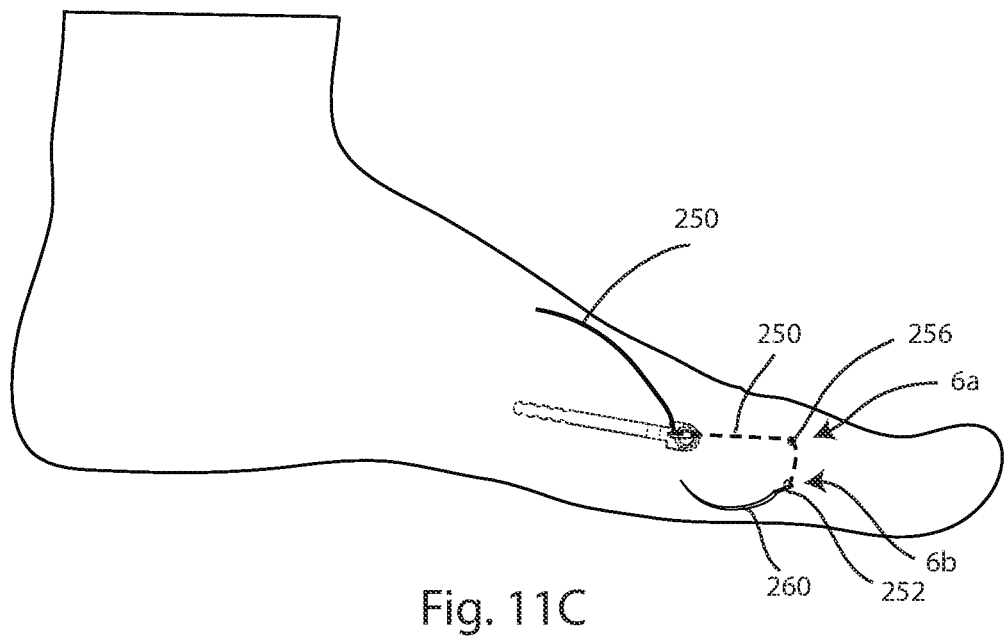
FIG. 11C is a medial view of the foot of FIG. 11B, with the needle emerging at a second location on the great toe.
Figure 11D:
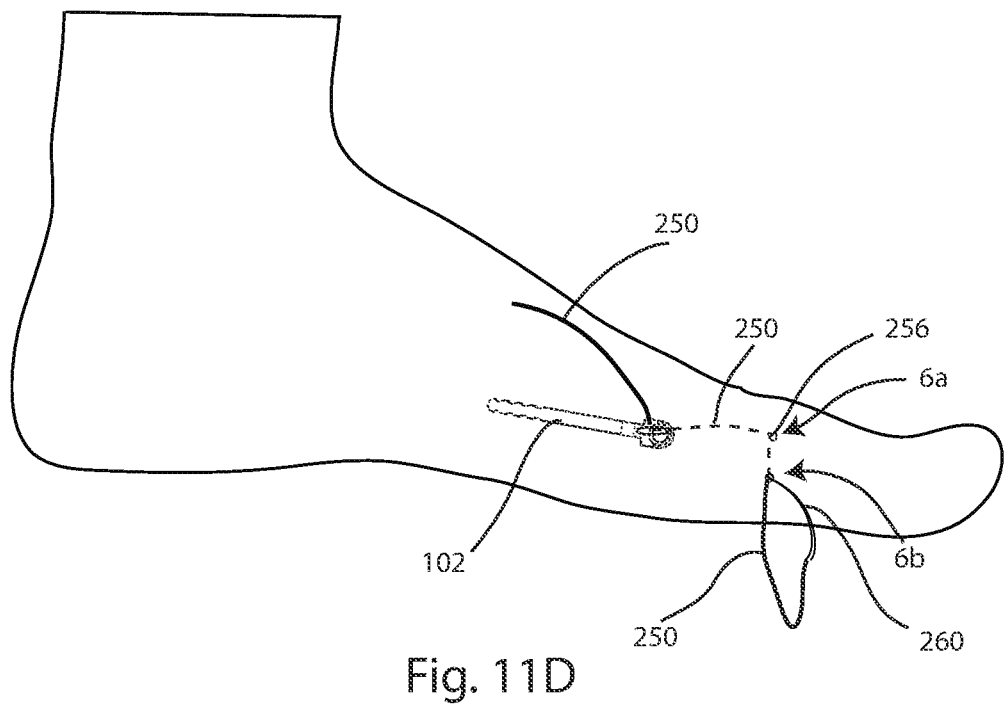
FIG. 11D is a medial view of the foot of FIG. 11C, with a second stitch being made at the second location on the great toe.
Figure 11E:
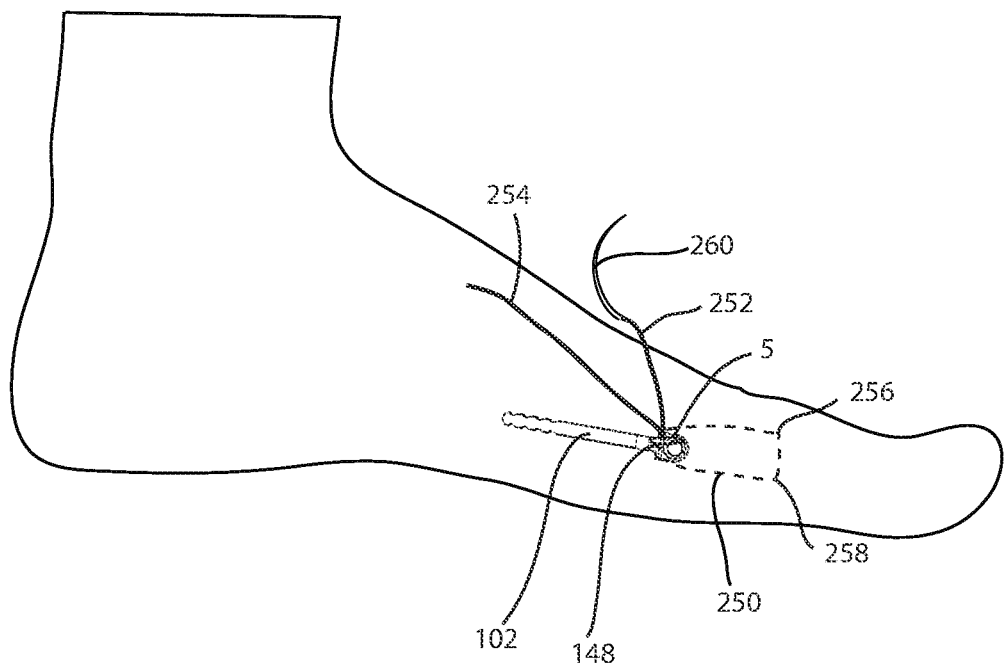
FIG. 11E is a medial view of the foot of FIG. 11D, with the suture routed through an implant bore, and the needle and suture emerging through the incision, and showing a path of the suture.

Referring to FIGS. 11A-11F and 12, the suture 250 may be engaged with implant 100 and secured to soft tissues of the great toe 6 to change the alignment of the phalanx 4 relative to the metatarsal 2 and correcting hallux valgus. As shown in FIG. 11A, a needle 260 carrying suture 250 is introduced through the incision 5, enters the medial capsule and emerges at a first location 6a on the epidermis of the great toe. The suture includes a first end 252 and a second end 254. As shown in FIG. 11B, the needle re-enters the skin at location 6a, creating a first stitch 256 in the soft tissue surrounding the phalanx 4. Continuing to FIG. 11C, the needle 260 and suture 250 emerge at a second location 6b on the epidermis of the great toe. Referring to FIG. 11D, the needle 260 and suture 250 re-enter the great toe at location 6b, creating a second stitch 258 in the soft tissue of the great toe 6. As shown in FIG. 11E, the needle and suture second end 252 emerge through the incision 5. The suture 250 is tensioned to change the alignment of the phalanx 4 relative to the metatarsal 2, providing tensile force along the medial side of the phalanx and correcting the hallux valgus. The nail shoulders 140, 142, abutting against the proximal metatarsal portion 2a act as a buttress to support the tension and alignment correction. The tensioned suture 250 is attached to the nail 102, with one or both of the first and second ends 252, 254 passing through the transverse bore 148. The suture first end 252 may pass through the transverse bore 148 from the inferior side 116 to the superior side 114 of the nail 102, and a knot 262 may be tied at the superior side of the bore 148, maintaining the suture tension and the correction. The knot 262 may be wider than the diameter of the transverse bore 148, so that the knot cannot pass through the bore. After knotting, the remaining suture free ends 252, 254 may be trimmed off. As seen in FIGS. 11E and 12, the suture 250 may follow a three-sided path from the implant 100 to the first and second stitches in the great toe, and back to the implant 100.

Referring to FIGS. 12 and 2, the screw tip 154 and shaft 152 are inserted through the nail opening 130 to secure the nail head 120 to the distal metatarsal portion 2b. As the shaft threads 158 engage in the bone, the nail head 120 lateral side 115 is urged to medial surface 2d of the distal metatarsal portion 2b. The screw head threads 156 engage with the nail opening threads 132 to lock the screw 104 to the nail 102. The incision 5 is closed. Following closure of the incision, the suture 250 remains secured to the great toe and attached to the implant 100.

Figure 17:
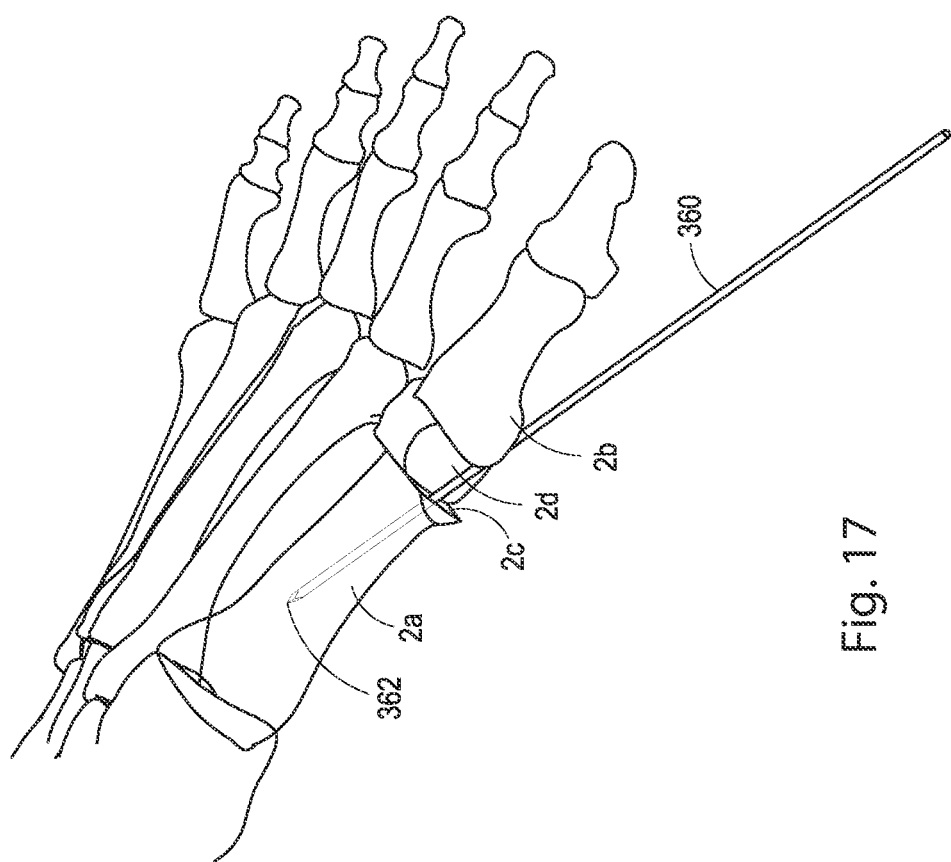
FIG. 17 is a perspective view of the foot skeleton of FIG. 9, showing the insertion of a k-wire into the proximal metatarsal portion.
Figure 21:
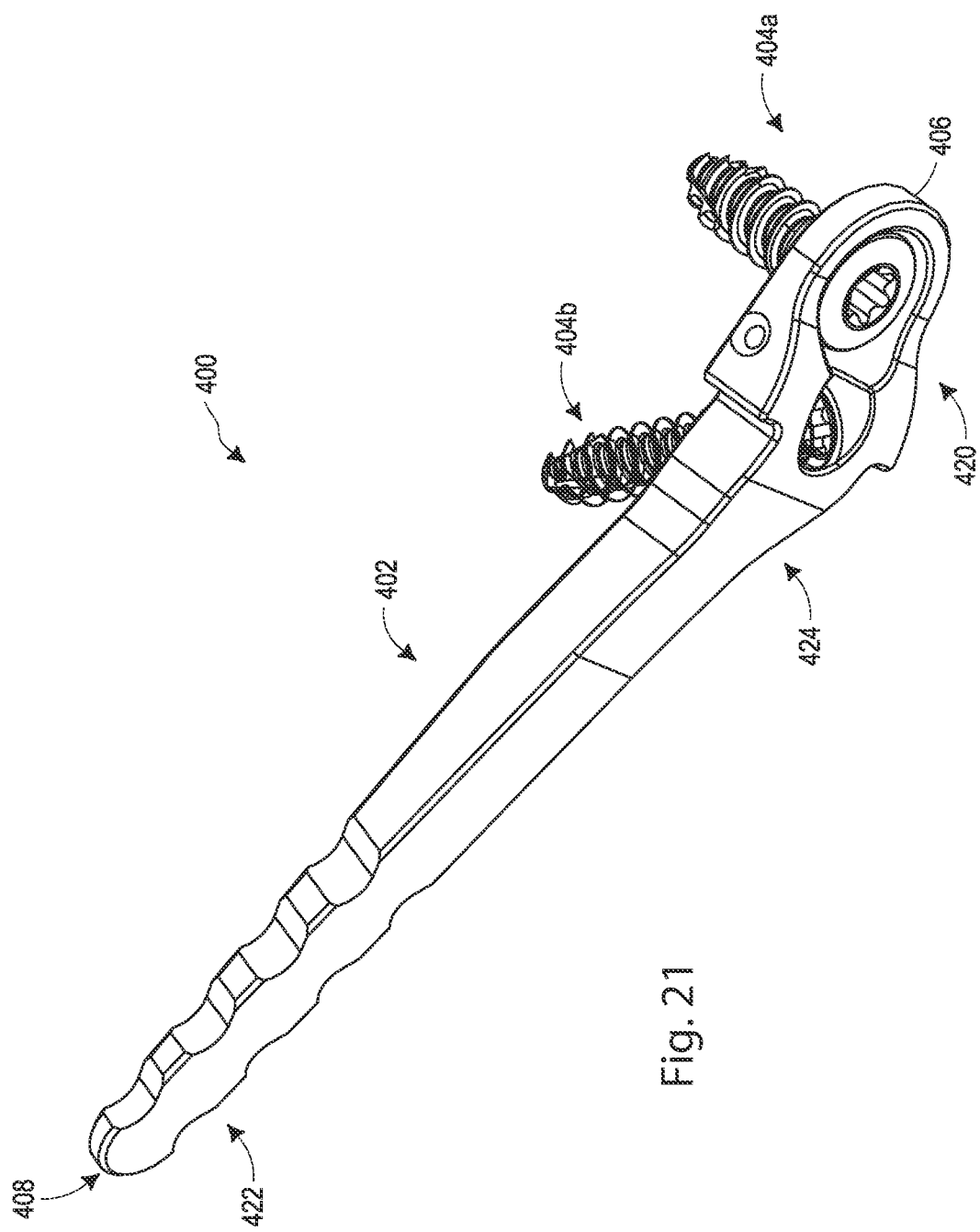
FIG. 21 is a perspective view of another bunion correction implant.
Figure 22:
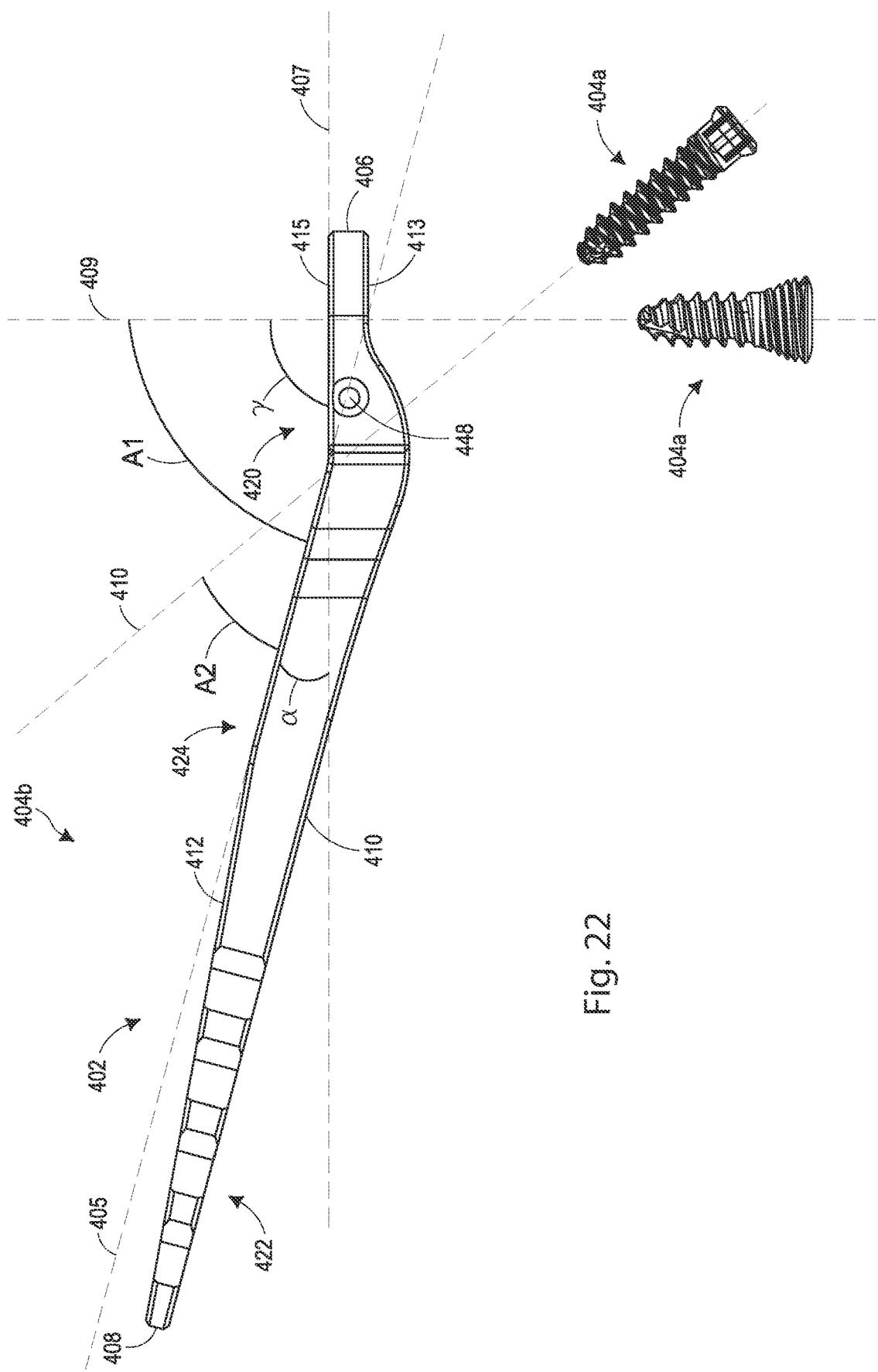
FIG. 22 is an exploded view of the implant of FIG. 21.
Figure 23:
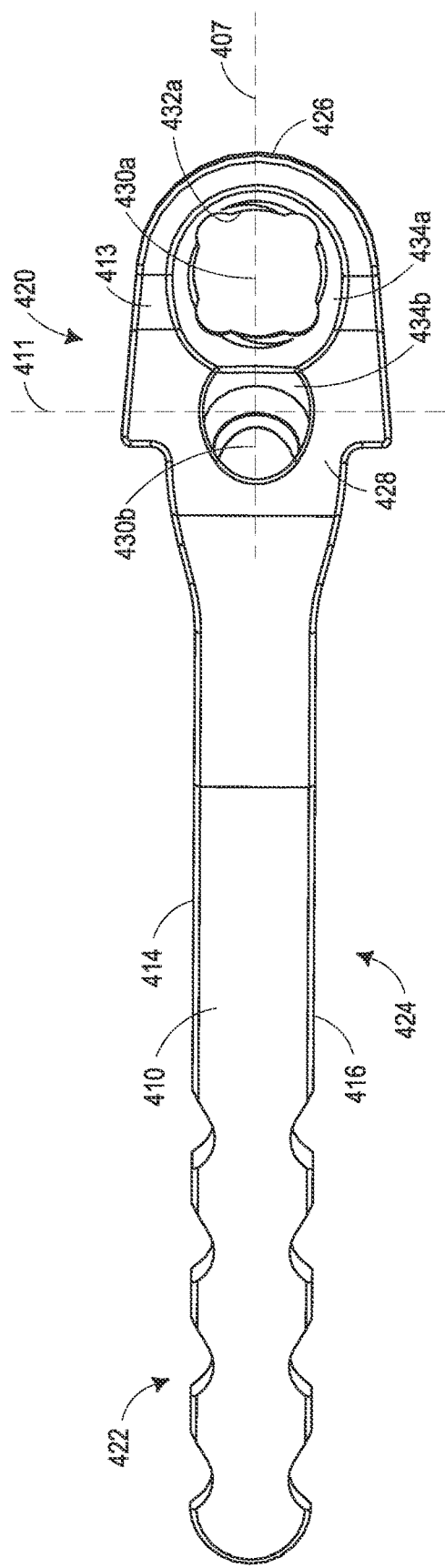
FIG. 23 is a medial view of a nail of the implant of FIG. 21.
Figure 24:
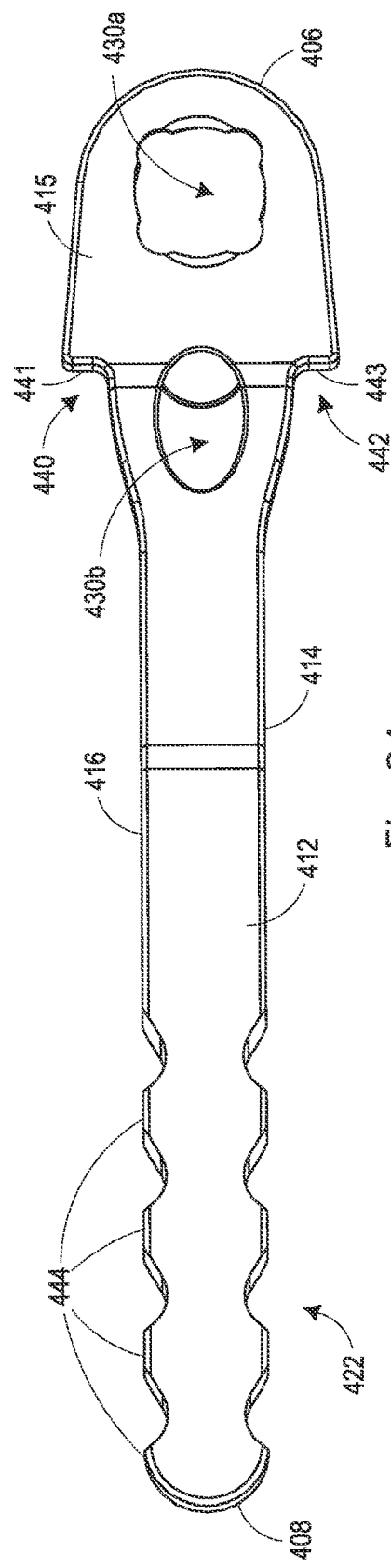
FIG. 24 is a lateral view of the nail of FIG. 23.
Figure 25:
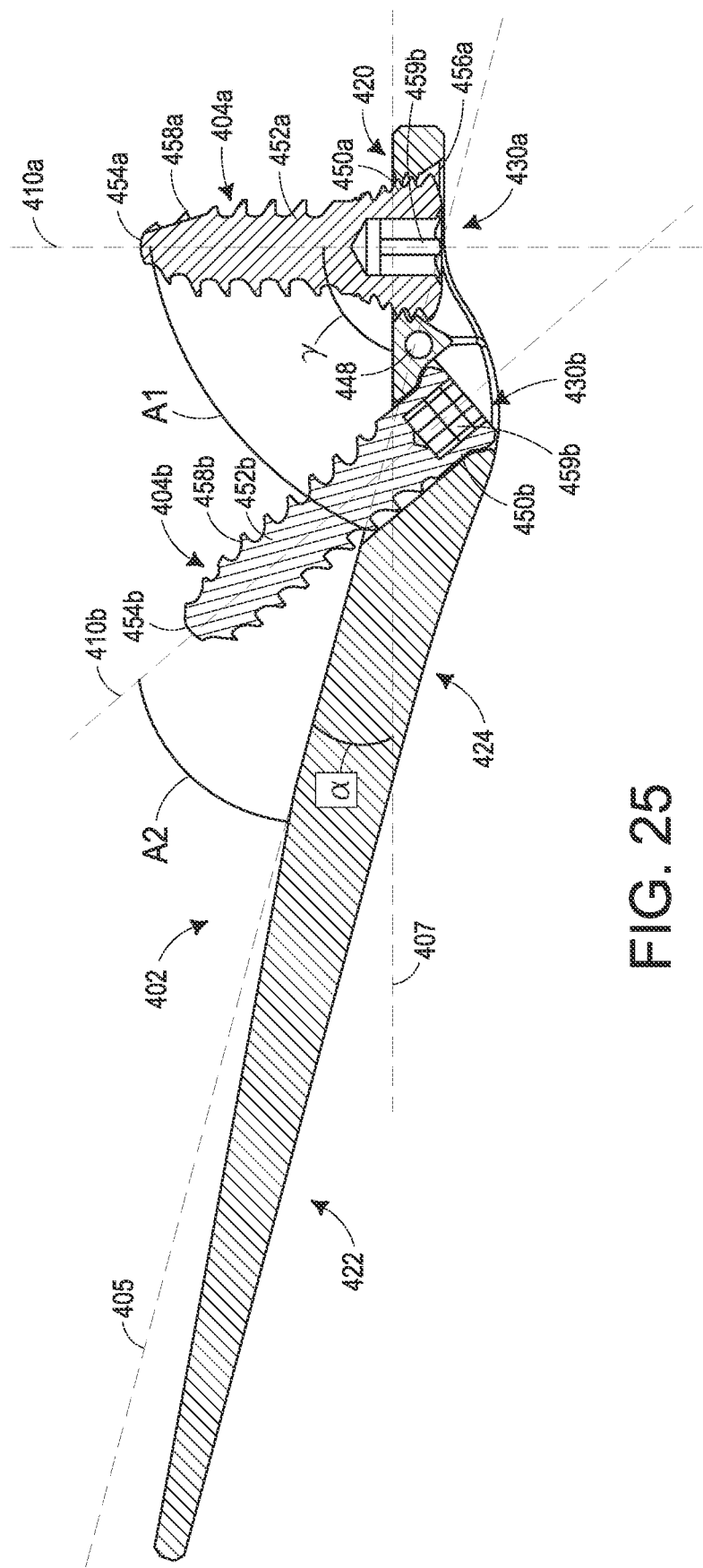
FIG. 25 is a section view of the implant of FIG. 21.
Figure 26:
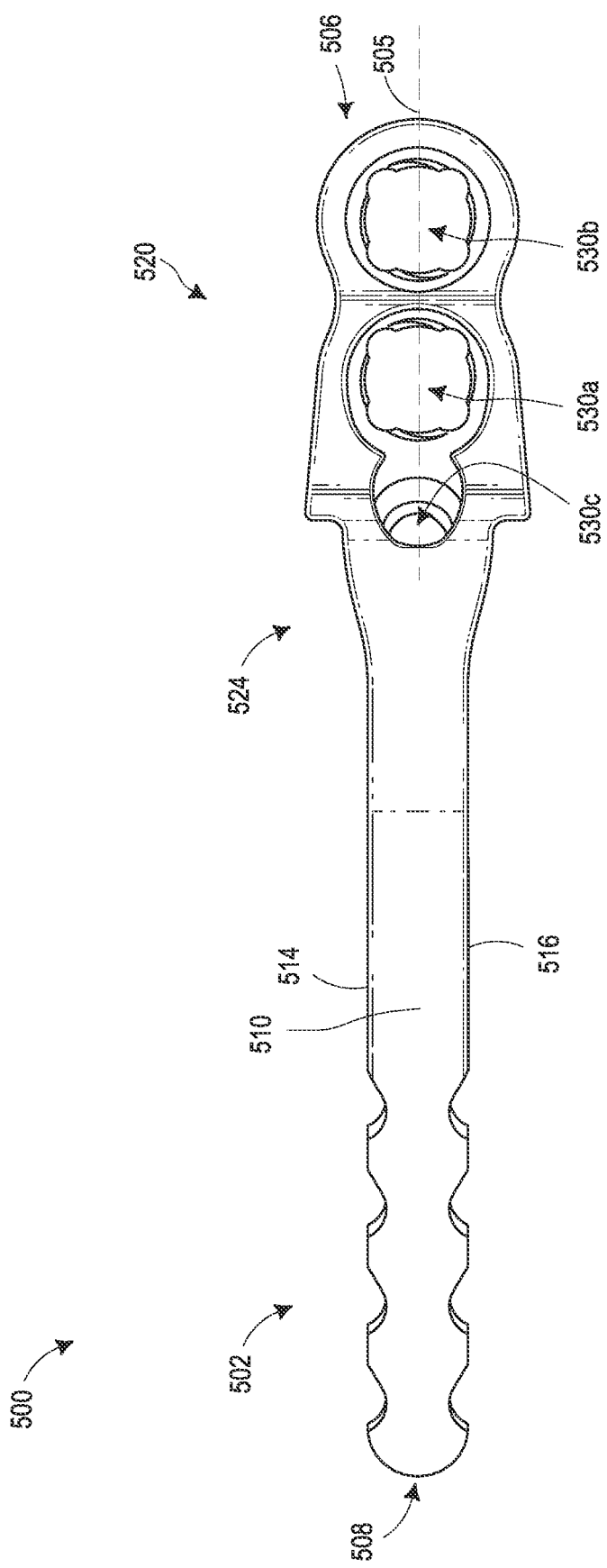
FIG. 26 is a medial view of a nail of another implant system.
Figure 27:
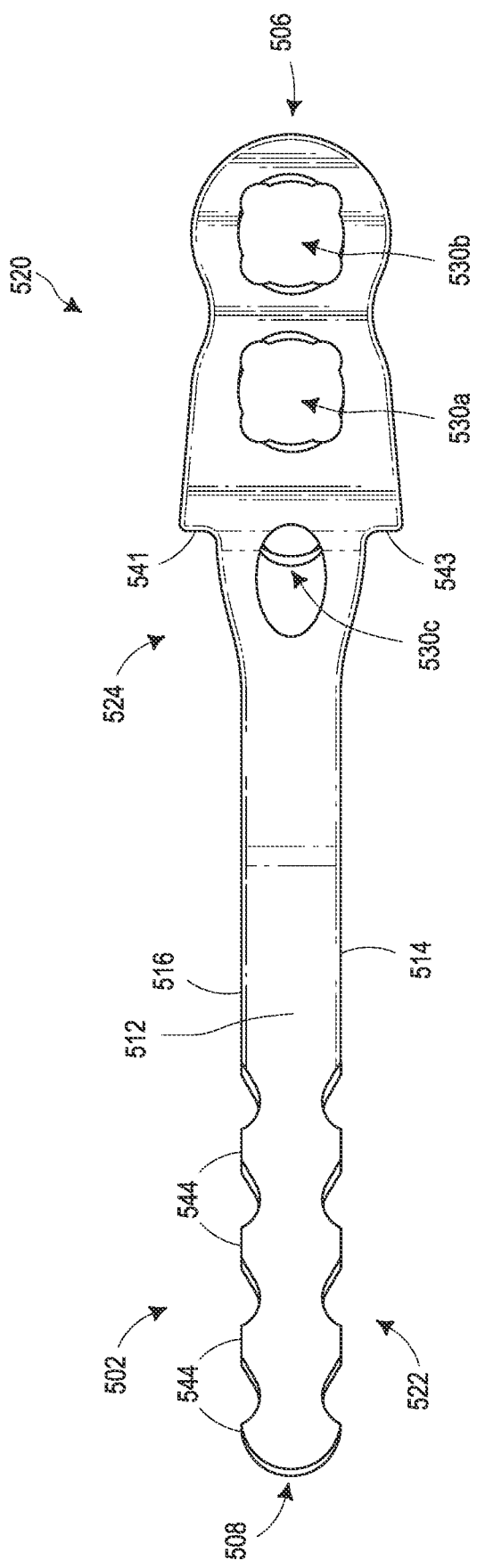
FIG. 27 is a lateral view of the nail of FIG. 26.
Figure 28:
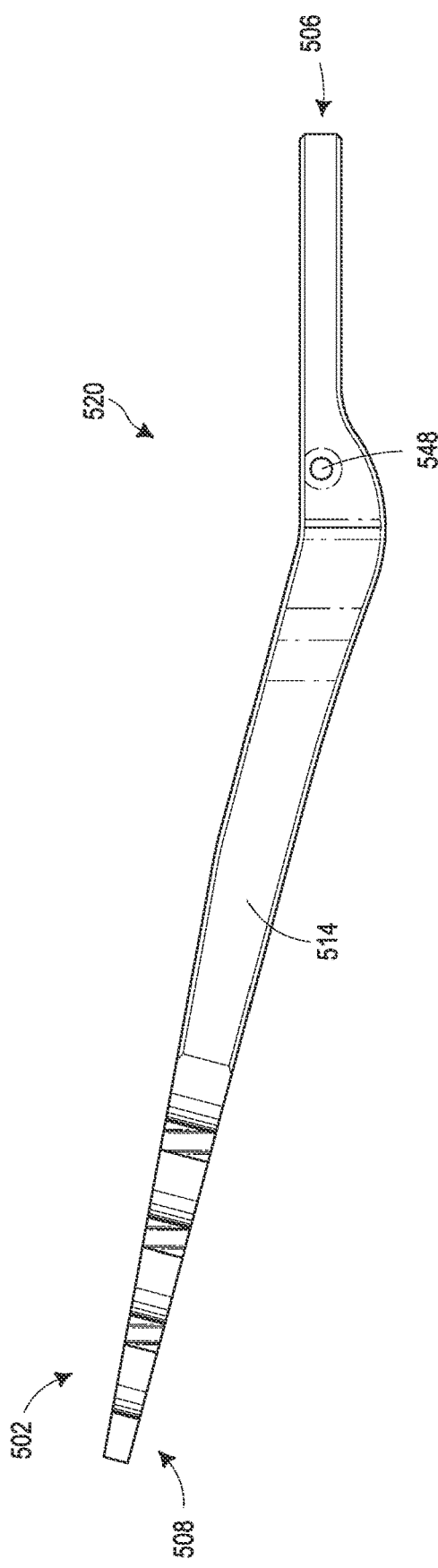
FIG. 28 is a superior view of the nail of FIG. 26.
Figure 29:
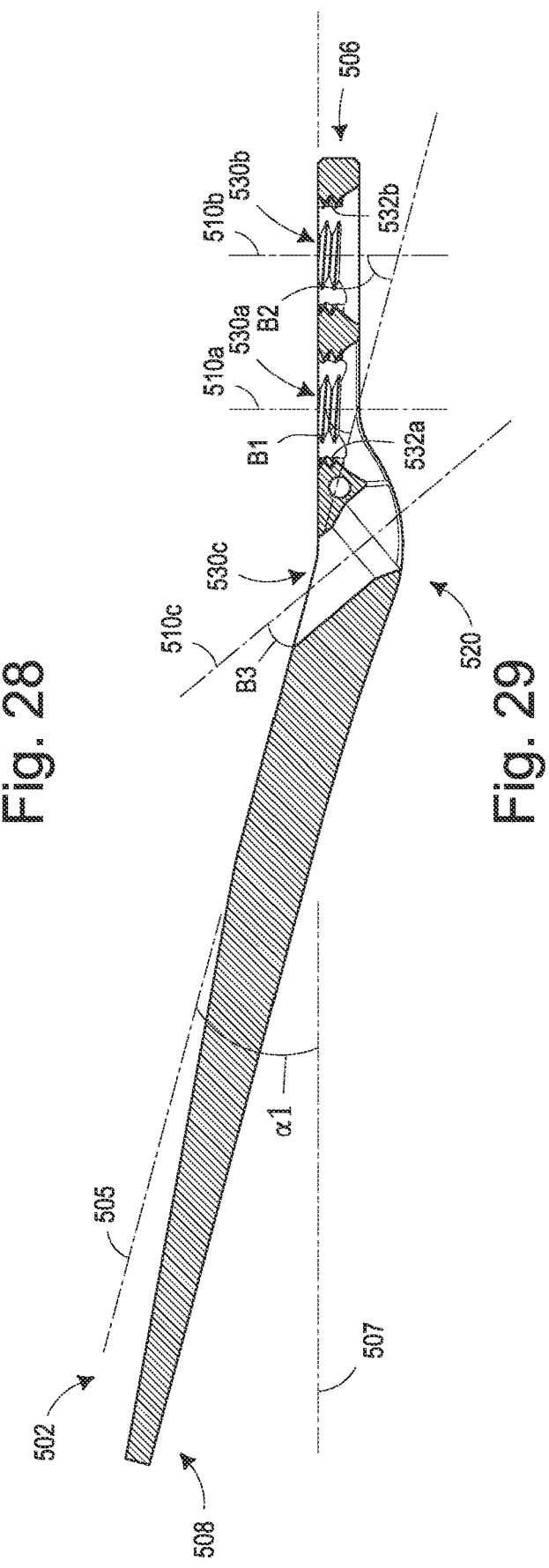
FIG. 29 is a section view of the implant of FIG. 26.

FIGS. 17-18 show an optional additional step in the insertion process for the bunion correction implant system 100 into a patient's foot, as shown and described in FIGS. 1-16 and the accompanying text. FIG. 17 shows the separate distal metatarsal portion 2b and the proximal metatarsal portion 2a before the insertion of the nail 102 into the proximal metatarsal portion 2a. The distal metatarsal portion 2b can include the medial facing surface 2d. The proximal metatarsal portion 2a can include the distal facing surface 2c. A k-wire 360 can be inserted into the proximal metatarsal portion 2a. The k-wire 360 can be inserted through the distal facing surface 2c. The k-wire 360 can include an end 362. The end 362 can include a sharpened point. The end 362 can be inserted into the intramedullary portion of the metatarsal 2. The k-wire 360 can be inserted into the proximal metatarsal portion 2a after the distal metatarsal portion 2b is shifted relative to the proximal metatarsal portion 2a (e.g., to expose the distal facing surface 2c).

The k-wire 360 can be inserted at an angle corresponding to the desired positioning of the implant 100 within the proximal metatarsal portion 2a. The entry point and/or the angle of entry of the k-wire 360 into the distal facing surface 2c can determine the amount of offset between the distal metatarsal portion 2b and the proximal metatarsal portion 2a. The k-wire 360 can accordingly be used to estimate the final positioning of the distal metatarsal portion 2b and the proximal metatarsal portion 2a. If the k-wire 360 is inserted in an undesirable position, the k-wire can be easily removed and repositioned within the proximal metatarsal portion 2a. The k-wire 360 can be used as a guide for a pocket instrument 320. As shown in FIG. 18, the pocket instrument 320 can be used to remove bone material from the proximal metatarsal portion 2a to form a pocket 380 for the nail 102. The nail 102 of the implant 100 can be inserted into the proximal metatarsal portion 2a (e.g., into the pocket 380) using the steps and/or tools described above in FIG. 10 and the accompanying text. The nail head 120 can be aligned and attached with the medially facing surface 2d of the distal metatarsal portion 2b.

As shown further in FIGS. 19-20, the pocket instrument 320 can include a handle 322. The pocket instrument 320 can include a insertion portion 326. The handle 322 can be generally aligned along a first axis 323. The insertion portion 326 can be generally aligned along a second axis 327. In one implementation, the first and second axes 323, 327 are parallel, although this is not required. The insertion portion 326 can be connected at the handle 322 by an offset neck 324. The offset neck 324 can space the handle portion 322 apart from the insertion portion 326.

The insertion portion 326 can be a broach, punch, or a non-rotating cutting instrument. The insertion portion 326 can include one or more cutting edges 330. The cutting edges 330 can be used to remove material from the proximal metatarsal portion 2a to form the pocket 380. Alternatively, the insertion portion 326 can be smoothed. The insertion portion 326 can include a tip 328. The insertion portion 326, whether smoothed or including the cutting edges 330, can be used to create a trial pocket for the nail 102. The shape of the pocket 380 can correspond to the shape of the nail 102 of the implant 100 (e.g., the insertion portion 326). The insertion portion 326 can include a lateral side 312 and a medial side 310. The insertion portion 326 can include a superior side 314 and an inferior side 316. The insertion portion 326 can be non-cylindrical in cross sectional shape (e.g., rectangular, as shown). The non-cylindrical in cross sectional shape can enhance stability of the nail 102 within the pocket 380. The pocket 380 (and/or the insertion portion 326) can be smaller, in one or more dimensions and/or along one or more sides, than the nail 102. The nail 102 can be in a press-fit condition within the pocket 380 (e.g., engaged with one or more opposing sides of the pocket 380) after insertion. In some implementations, the aperture 380 and insertion portion 326 can be sized to the dimensions of the nail 102.

The insertion portion 326 can include a channel 340. The channel 340 can extend along the second axis 327 of the insertion portion 326. The channel 340 can include a proximate opening 342 and a distal opening 344. The proximal opening 342 can be adjacent to the offset neck portion 324. The distal opening 344 can be adjacent to the tip 328.

In use to form the pocket 380, the insertion portion 326 of the pocket instrument 320 can be guided into the proximal metatarsal portion 2a along the k-wire 360. The offset neck 324 can space the handle portion 322 from the k-wire 360 to improve the ergonomics of the pocket instrument 320. The k-wire 360 can be received within the channel 340. The pocket instrument 320 can be slid along a length of the k-wire 360 into the proximal metatarsal bone portion 2a. The pocket instrument 320 can be moved in one or more sawing strokes or impacts (e.g., from a hammer striking the pocket instrument 320) to form the pocket 380. After forming the pocket 380, the k-wire 360 and the insertion portion 326 can be removed from the proximal metatarsal portion 2a. This implant system 100 can be installed within the pocket 380, as described above.

Referring to FIGS. 21-25, a bunion correction implant system 400 according to another embodiment of the invention includes a nail 402, a first fastener 404a, and a second fastener 404b. The nail 402 may be implanted to extend longitudinally into the proximal metatarsal portion 2a of the resected metatarsal 2. The first fastener 404a can be inserted through a first portion of the nail 402 to secure it to the distal metatarsal portion 2b of the metatarsal 2. The second fastener 404b can be inserted through a second portion of the nail 402 to secure it to the proximal metatarsal portion 2a of the metatarsal 2. The implant system 400 may further include a suture which may be routed through the medial capsule of the MTP joint, secured in the soft tissues of the great toe, tensioned to re-align the position of the proximal phalanx 4 relative to the metatarsal, and/or secured to the nail, as described above in relation to FIGS. 1-20 and the accompanying description.

The implant nail 402 can be a monolithic body extending from a first end 406 which may be a distal end, to a second end 408 which may be a proximal end. The nail 402 may be generally rectangular in cross-section. The nail 402 can have a medial side 410 which may be an outer side, a lateral side 412 which may be an inner side, a superior side 414, and/or an inferior side 416. The nail 402 can include a head 420. The head 420 can be one the first end 406. The nail 402 can include an anchor 422. The anchor 422 can be on the second end 408. The nail 402 can include a neck 424. The neck 424 can extend between the head 420 and the anchor 422.

The nail anchor 422 and neck 424 can extend along an implant axis 405. The nail head 420 can extend distally away from the neck 424 at an angle α. The nail head 420 can extend between a head first end 426 and a head second end 428 along a head first axis 407. The angle α between the neck lateral surface and the head lateral surface can be approximately 25°. In other implementations of the invention, angle α may be in the range of 0° to 90°. Desirably, the angle α may be in the range of 0° to 60°. Desirably, the angle α may be in the range of 15° to 60°. In at least the embodiment depicted, the nail 402 and assembled implant 400 are bilaterally symmetrical with respect to the implant axis 405, and with respect to the head first axis 407.

The nail head 420 includes a first opening 430a. The first opening 430a can be centered on the nail head 420. The first opening 430a can extend along a head second axis 410a. The head second axis 410a can be at an angle A1 to the implant axis 405. The angle A1 can be between approximately 0° and 135°. Desirably, the angle A1 may be in the range of 30° to 60°. The head second axis 410a may extend generally medially-laterally (ML) upon implantation. The first opening 430a can extend between a head lateral side 415 and a head medial side 413. The first opening 430a can include threads 432a for engagement with the first fastener 404a. Other implementations may lack threads. A concave lip 434a can encircle the first opening 430. The head second axis 410a can be at an angle 7 with the head first axis 407. Angle 7 can be approximately 90°. Desirably, the angle 7 may be in the range of 45° to 135°.

The nail 402 can include a second opening 430b. The second opening 430b can be on the nail head 420 and/or the neck 424. The second opening 430b can be centered on a head third axis 410b. The second opening 430b can extend between the head lateral side 415 and the head medial side 413. The head third axis 410b can be at an angle A2 to the implant axis 405. The angle A2 can be less than approximately 45°. Desirably, the angle A2 may be in the range of 0° to 90°. Desirably, the angle A2 may be in the range of 30° to 60°. The second opening 430b can include concave lip 434b. In some implementations, the second opening 430b can include threads (not shown) for engagement with the second fastener 404b.

The head second end 428 can be wider than the neck 424 with respect to the superior-inferior dimension. The head second end 428 can include a first shoulder 440 and a second shoulder 442. The shoulders 440, 442 can project superiorly and inferiorly, respectively, away from the neck 424 at the intersection of the neck 424 and the head 420. The first shoulder 440 can include a first proximal shoulder surface 441. The second shoulder 442 can include a second proximal shoulder surface 443. The proximal shoulder surfaces 441, 443 can face proximally away from the head 420. The proximal shoulder surfaces 441, 443 can be at right angles to the neck superior and inferior sides 414, 416.

The head 420 can include a transverse bore 448. The transverse bore 448 can extend along a head fourth axis 411 which is perpendicular to the head first axis 407 and the head second axis 410a. The head fourth axis 411 can extend generally superiorly-inferiorly (SI) upon implantation. The thickness of the head 420 between the medial 413 and lateral 415 sides can increase between the head first end 426 and the head second end 428 so that the thickest part of the head 420 is at the shoulders 440, 442. A greater thickness of the head 420 between the medial 413 and lateral 415 sides can shift the head 420 further outwardly with respect to a medial axis of the proximal metatarsal portion 2a. The transverse bore 448 can extend through the thickest part of the head 420.

The neck 424 can extend between and connect the head 420 with the anchor 422. The thickness of the neck 424 between the medial and lateral sides 410, 412 can vary depending on the desired degree of shift of the metatarsal. The neck thickness can taper between the head 420 and the anchor 422. The width of the neck 424 between the superior 414 and inferior 416 sides may also vary. The length of the nail 402 between the first and second ends 406, 408 can vary, as can the relative lengths of the head, neck, and/or anchor portions. The anchor 422 can be coaxial with the neck 424. The anchor 422 can extend from the neck 424 to the second end 408 of the nail 402. Both the thickness of the anchor 422 between the medial and lateral sides 410, 412, and the width of the anchor 422 between the superior 414 and inferior 416 sides can taper towards the nail second end 408. This can promote easy insertion of the nail 402 into metatarsal 2.

The anchor 422 at its second end 408 can be rounded, pointed, flattened, serrated, or another shape. The anchor 422 can include a plurality of bone engagement features 444 which may be shaped as teeth, scallops, serrations, or other shapes to promote engagement within bone. The neck 424 and anchor 422 can be free from or include openings for supplementary fixation or instrument connection.

Fastener 404a can include a fastener head 450a, driving feature 459a, fastener shaft 452a, tip 454a, threads 456a for locking engagement with threads in the nail head 420 (e.g., opening 430a), and/or threads 458a for engagement in bone. Fastener 404b can include a fastener head 450b, driving feature 459b, fastener shaft 452b, tip 454b and/or threads 458b for engagement in bone. The fasteners 404a/404b can be locking screw type fasteners; in other implementations the fasteners 404a/404b can be locking or non-locking, and may be polyaxially adjustable or non-polyaxially adjustable. The nail 402 and fasteners 404a/404b may comprise titanium, stainless steel, PEEK, nitinol, and/or other rigid biocompatible materials or combinations thereof.

The implant system 400 can be used in place of the implant system 100 in the insertion process into a patient's foot as shown and described in FIGS. 1-20 and the accompanying text. The implant system 400 can require the following further steps to anchor the nail 402 into the prepared proximal metatarsal portion 2a.

An implant inserter such as the inserter 240 may be employed to implant the nail 402 into the proximal metatarsal portion 2a. The implant engagement end 246 can cooperate with the openings 430a and/or 430b or otherwise with the nail 402. The implant engagement end 246 can include threads 248 that can engage with nail threads 432a (or nail threads in the second opening 430b) to removably attach the nail 402 to the inserter 240. The inserter 240 is moved to insert the anchor 422 and neck 424 proximally into the distal-facing surface 2c and into the intramedullary canal of the metatarsal 2. Desirably, the engagement end 246 can cooperate with the opening 430b, which can more closely align the inserter 240 with the anchor 422 and neck 424. Accordingly, the inserter 240 can be used to apply force more directly into the proximal metatarsal portion 2a as the anchor 422 and neck are inserted.

The head 420 can be left distal to the proximal metatarsal portion 2a. If needed, the inserter 240 may be tapped to drive the nail 402 into position in the proximal metatarsal portion 2a. The nail 402 can be positioned so that the proximal surfaces 441, 443 of shoulders 440, 442 abut the distal-facing surface 2c of the metatarsal. The nail head lateral side 415 can be immediately adjacent to medial surface 2d of the distal metatarsal portion 2b. With the nail 402 seated in the desired location, the inserter 240 can be rotated to disengage it from the implanted nail 402.

The fastener 404b can fasten the nail 402 with the proximal metatarsal portion 2a. A driver (e.g., screwdriver) can be employed to implant the fastener 404b. The driver can couple with the driving feature 459b. The tip 454b and shaft 452b can be inserted into the second opening 430b. The fastener 404b can be rotated to engage the threads 458b with the proximal metatarsal portion 2a. The installation of the fastener 404b can advantageously secure the position of the nail 402 relative to the metatarsal 2. Accordingly, the suturing steps and alignment of the distal metatarsal portion 2b relative to the nail 402 as shown in FIGS. 11A-12 and described in the accompanying description can be performed more accurately.

Referring to FIGS. 26-29, a bunion correction implant system 500 according to another embodiment of the invention includes a nail 502. The implant system 500 can be used in place of the implant system 400 in the insertion process into a patient's foot as shown and described above. The nail 502 may be implanted to extend longitudinally into the proximal metatarsal portion 2a of the resected metatarsal 2. The nail 502 can be fixed with fasteners in the manner similar to the fasteners 404a, 404b described above.

The implant nail 502 can be a monolithic body extending from a first end 506 which may be a distal end, to a second end 508 which may be a proximal end. The nail 502 can have a medial side 510 which may be an outer side, a lateral side 512 which may be an inner side, a superior side 514, and/or an inferior side 516. The nail 502 can include a head 520. The head 520 can be one the first end 506. The nail 502 can include an anchor 522. The anchor 522 can be on the second end 508. The nail 502 can include a neck 524. The neck 524 can extend between the head 520 and the anchor 522.

The nail anchor 522 and neck 524 can extend along an implant axis 505. The nail head 520 can extend distally away from the neck 524 at an angle α1 along head axis 507. The angle α1 between the neck lateral surface (along axis 505) and the head lateral surface (along head axis 507) can be approximately 25°. In other implementations of the invention, angle α1 may be in the range of 0° to 90°. Desirably, the angle α1 may be in the range of 0° to 60°. Desirably, the angle α1 may be in the range of 15° to 60°. In at least the embodiment depicted, the nail 502 and assembled implant 500 are bilaterally symmetrical with respect to the implant axis 505.

The nail head 520 includes a first opening 530*a* and a second opening 530*b*. The first and second head openings 530*a*, 530*b* can extend along respective first and second axes 510*a*, 510*b*. The first axis 510*a* can be at an angle B1 to the implant axis 505. The second axis 510*b* can be at an angle B2 to the implant axis 505. Angle B1 and B2 can be equal, although this is not required. The angles B1, B2 can be between approximately 0° and 135°. Desirably, the angles B1, B2 may be in the range of 30° to 90°. The axes 510*a*, 501*b* may extend generally medially-laterally (ML) upon implantation. The first and second openings 530*a*, 530*b* can extend between a head lateral side and a head medial side. The first and second openings 530*a*, 530*b* can include threads 532*a*, 532*b* for engagement with fasteners. Other implementations may lack threads. A concave lip can encircle the respective first and second openings 530*a*, 530*b*. The first and/or second axes 510*a*, 510*b* can be at perpendicular to the axis 507.

The nail 502 can include a third opening 530*c*. The third opening 530*c* can be on the nail head 520 and/or the neck 522. The third opening 530*c* can be centered on a third axis 510*c*. The third opening 530*c* can extend between the head lateral side and the head medial side. The head third axis 510*c* can be at an angle B3 to the implant axis 505. The angle B3 can be less than approximately 45°. Desirably, the angle B3 may be in the range of 0° to 90°. Desirably, the angle B3 may be in the range of 30° to 60°. The third opening 530*c* can include a concave or tapered up lip. In some implementations, the third opening 530*c* can include threads (not shown) for engagement with a fastener.

The neck 524 can extend between and connect the head 520 with the anchor 522. The neck 524 and/or anchor 522 may be generally rectangular in cross-section. The anchor 522 can extend from the neck 524 to the second end 508 of the nail 502. Both the thickness of the anchor 522 between the medial and lateral sides 510, 512, and the width of the anchor 522 between the superior 514 and inferior 516 sides can taper towards the nail second end 508. This can promote easy insertion of the nail 502 into metatarsal 2. The head 520 can include a transverse bore 548. The transverse bore 548 can extend generally superiorly-inferiorly (SI) upon implantation.

The anchor 522 at its second end 508 can be rounded, pointed, flattened, serrated, or another shape. The anchor 522 can include a plurality of bone engagement features 544 which may be shaped as teeth, scallops, serrations, or other shapes to promote engagement within bone. The neck 524 and anchor 522 can be free from or include openings for supplementary fixation or instrument connection.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The terms "approximately," "about," and "substantially" as used herein represent an amount close to the stated amount that still performs a desired function or achieves a desired result. For example, in some embodiments, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees. Given ranges are inclusive of endpoints.

What is claimed is:

1. An implant nail for correcting a bunion formed at a joint between a metatarsal and a great toe, the implant nail comprising:
    a monolithic body comprising:
        a head at a first end of the monolithic body, the head having a bone-facing surface and an outer surface opposite the bone-facing surface, the head comprising:
            a head first end including a shoulder;
            a head second end;
            a transverse bore extending along a superior-inferior axis of the head, the transverse bore disposed closer to the bone-facing surface than the outer surface; and a first bone fixation hole extending through the head, the first bone fixation hole oriented along a first hole axis;

an anchor at a second end of the monolithic body; and a neck disposed between the second head end and the anchor, the neck comprising a second bone fixation hole extending through the neck, the second bone fixation hole oriented along a second hole axis, the second hole axis being off-axis from the first hole axis.

2. The implant nail of claim 1, wherein an implant axis of the anchor forms a first angle with a head axis of the head, the first angle being less than 90°.

3. The implant nail of claim 2, wherein the implant axis forms a second angle with the second hole axis, the second angle being between 30° and 60.

4. The implant nail of claim 3, wherein the first angle between the implant axis and the head axis is in the range of 15° to 60°.

5. The implant nail of claim 3, wherein the first hole axis is perpendicular to a plane defined by a lateral side of the head.

6. The implant nail of claim 3, wherein the first and second angles are in a plane parallel with a superior side of the nail.

7. The implant nail of claim 3, wherein the shoulder includes superior and inferior portions extending at right angles to respective superior and inferior sides of the neck.

8. The implant nail of claim 3, wherein the second bone fixation hole is configured to receive a second fastener such that a head of the second fastener is fully recessed within the neck.

9. The implant nail of claim 3, wherein the first and second angles are measured in a plane parallel with a superior view of the implant.

10. The implant nail of claim 1, wherein the first bone fixation hole diverges away from the second bone fixation hole as the first bone fixation hole extends from the outer surface to the bone-facing surface.

11. The implant nail of claim 10, wherein the transverse bore is disposed between the first and second bone fixation holes.

12. The implant nail of claim 11, wherein the first and second bone fixation holes intersect each other at the outer surface.

13. The implant nail of claim 1, wherein the first and second bone fixation holes are aligned with each other along a length of the implant nail.

14. The implant nail of claim 13, wherein the first and second bone fixation holes are the only bone fixation holes of the implant nail.

* * * * *